United States Patent [19]
Alig et al.

[11] Patent Number: 5,273,982
[45] Date of Patent: Dec. 28, 1993

[54] ACETIC ACID DERIVATIVES

[75] Inventors: Leo Alig, Kaiseraugst; Albrecht Edenhofer, Riehen; Marcel Müller, Frenkendorf, all of Switzerland; Arnold Trzeciak, Schopfheim, Fed. Rep. of Germany; Thomas Weller, Basel, Switzerland

[73] Assignee: Hoffmann-La Roche Inc., Nutley, N.J.

[21] Appl. No.: 665,110

[22] Filed: Mar. 5, 1991

[30] Foreign Application Priority Data

Mar. 9, 1990 [CH] Switzerland ............ 775/90
Jan. 17, 1991 [CH] Switzerland ............ 115/91
Jan. 23, 1991 [CH] Switzerland ............ 192/91

[51] Int. Cl.$^5$ ............ A01N 43/40; C07D 207/00
[52] U.S. Cl. ............ 514/315; 514/316; 514/318; 514/326; 544/360; 544/364; 544/365; 544/372; 546/186; 546/189; 548/530; 548/539
[58] Field of Search ............ 546/189, 186; 544/365, 544/372, 364, 360; 548/539, 530; 514/315, 316, 326, 318

[56] References Cited

U.S. PATENT DOCUMENTS 4,578,079 3/1986 Ruoslahti et al. ............ 623/11

FOREIGN PATENT DOCUMENTS 183271 11/1985 European Pat. Off. .

OTHER PUBLICATIONS

Derwent 51899 B Jun. 5, 1979.
Derwent 88-206834 Jun. 25, 1987.
Chem. Abstract 101:55522f 1987.
Chemical Abstract 103:209699z (1985).
Chemical Abstract 92:208785s (1980).

*Primary Examiner*—C. Warren Ivy
*Assistant Examiner*—Raymond Covington
*Attorney, Agent, or Firm*—George M. Gould; William H. Epstein; Patricia S. Rocha

[57] ABSTRACT

Acetic acid derivatives of formula $$H_2N(NH)C-X-Y-CO-Z-CH(Q^1)COOQ^2 \quad I$$

and hydrates, solvates and physiologically acceptable salts thereof are useful to inhibit the binding of adhesive proteins to blood platelets and also to inhibit blood platelet aggregation and cell-cell adhesion.

10 Claims, No Drawings

ACETIC ACID DERIVATIVES

1. SUMMARY OF THE INVENTION

The present invention relates to new acetic acid derivatives, to processes for their preparation, to pharmaceutical preparations which contain such compounds, and to the use of these compounds for the production of pharmaceutical preparations.

2. DETAILED DESCRIPTION OF THE INVENTION

In particular the invention relates to acetic acid derivatives of the formula $$H_2N(NH)C-X-Y-CO-Z-CH(Q^1)COOQ^2 \quad (I)$$

in which $Q^1$ is hydrogen, methyl or phenyl, $Q^2$ is hydrogen, phenyl-lower alkyl or lower alkyl which can be cleaved under physiological conditions, X is 1,4-phenylene, 1,4-piperidinylene bound via the C atom in the 4-position to the group Y, or 2,5- or 3,6-pyridylene Y is a group of the formula $-(CH_2)_{0-2}-CONHCH(Q^3)(CH_2)_{1-3}-$     (Y$^1$)

$-CONHCH_2CH(Q^4)-$     (Y$^2$)

$-(CH_2)_2NHCOCH_2-$     (Y$^3$)

$-NHCO(CH_2)_3-$     (Y$^4$)

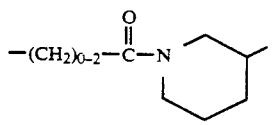     (Y$^5$)

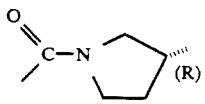     (Y$^6$)

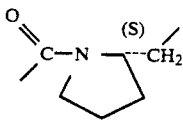     (Y$^7$)

$Q^3$ is hydrogen, methyl, phenyl, —COOH, —COO—lower alkyl, —CONH(CH$_2$)$_2$—COOH or —CONH(CH$_2$)$_2$—COO—lower alkyl, $Q^4$ is hydrogen, methyl or phenyl, Z is a 1,4-piperazinylene group, a 1,4-piperidinylene group bound via the N-atom in the 1-position to the CO group, or a group of the formula $-NHCH(R^1)-$ or $-NHCH(COR^2)-$ $R^1$ is hydrogen, methyl, phenyl or —COO—lower alkyl, $R^2$ is the radical of an α-aminocarboxylic acid bound via the amino group or an ester or amide thereof, or a group of the formula —NHCH$_2$CH$_2$—Ar, or —CO—R$^2$ is an optionally mono- or di-lower-alkylated carbamoyl group or a pyrrolidinoyl or piperidinoyl group, Ar is phenyl or phenyl which is substituted by lower alkyl, lower alkoxy, —COOH, —COO—lower alkyl, —O(CH$_2$)$_{1-4}$—COOH, —O(CH$_2$)$_{1-4}$—COO—lower alkyl, —CONH$_2$, —CONH-lower alkyl, —CON(lower alkyl)$_2$, pyrrolidinoyl or piperidinoyl, and hydrates or solvates and physiologically utilisable salts thereof.

In the context of the present invention, tBu denotes t-butyl, Boc denotes t-butoxycarbonyl, Z denotes benzyloxycarbonyl, Val denotes L-valyl, Phe denotes L-phenylalanyl, Ser denotes L-seryl, Gly denotes glycyl, Ala denotes L-alanyl, Asp denotes L-α-aspartyl, Leu denotes L-leucine and Tyr denotes L-tyrosine.

The expression "lower" denotes groups having 1-6, preferably 1-4, C atoms. Examples of lower alkyl groups are methyl, ethyl, propyl, isopropyl and n-, s- or t-butyl. Examples of lower alkyl groups which can be cleaved under physiological conditions are primary and secondary lower alkyl groups.

Examples of α-aminocarboxylic acid radicals bound via the amino group are Val, Phe; Ser, Leu, Tyr and their corresponding lower alkyl or phenyl-lower alkyl esters, amides and mono- or di-lower alkyl amides.

The compounds of the formula I can be solvated, in particular hydrated. Hydration can take place in the course of the preparation process or occur gradually as a consequence of hygroscopic properties of an initially anhydrous compound of the formula I.

Examples of physiologically utilisable salts of the compounds of the formula I are salts with physiologically tolerable mineral acids, such as hydrochloric acid, sulphuric acid or phosphoric acid, or with organic acids, such as methanesulphonic acid, acetic acid, trifluoroacetic acid, citric acid, fumaric acid, succinic acid or salicylic acid. The compounds of the formula I can also form salts with physiologically tolerable bases. Examples of such salts are alkali metal, alkaline earth metal, ammonium and alkylammonium salts, such as the Na, K, Ca or tetramethylammonium salt. The compounds of the formula I contain an amidino group and can therefore be present in the form of zwitterions.

The compounds of the formula I, which contain one or more asymmetric C atoms, can be present as enantiomers, as diastereomers or as mixtures thereof, for example as racemates.

Preferred compounds of the formula I are those of the formula $$H_2N(HN)C-X-Y^a-CONHCH(R^{11})CH_2COOQ^{21} \quad I\text{-}A$$

in which

X is 1,4-phenylene or 1,4-piperidinylene bound via the C atom in the 4-position to the group Y$^a$, Y$^a$ is a group of the formula $-(CH_2)_{0-1}-CONHCH(Q^a)(CH_2)_{1-2}-$     (Y$^{11}$)

$-(CH_2)_2NHCOCH_2-$     (Y$^3$)

$-NHCO(CH_2)_3-$     (Y$^4$)

or

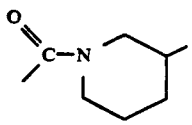 (Y⁵¹)

$Q^a$ is hydrogen or phenyl,
$R^{11}$ is hydrogen or —CO—$R^{22}$,
$R^{22}$ is the radical of an α-aminocarboxylic acid bound via the amino group or of an ester or amide thereof, and
$Q^{21}$ is hydrogen or lower alkyl which can be cleaved under physiological conditions.

In the formula I, Y is preferably a group of the formula $Y^1$, in particular
—CONH(CH₂)₂₋₄—,
—CH₂CONH(CH₂)₂—,
—CONHCH(C₆H₅)CH₂—,
—CONHCH(CONHCH₂CH₂COOH)CH₂—,
—CONHCH(COOH)CH₂— or
—CONHCH(CH₃)CH₂—.

In the formula I,Z is preferably a group of the formula —NHCH₂—, —NHCH(CH₃)—, —NHCH(C₆H₅)—, —NHCH(COO-isobutyl)—, —NHCH(CO—Val)—, —NHCH(CO-Phe)—, —NHCH(CO-Tyr)—, —NHCH(CO-Ser-OC₂H₅)—, —NHCH(CO-Leu-O-isopropyl)-, —NHCH(CONHCH₂CH₂—C₆H₄—OCH₃)—, —NHCH(CONHCH₂CH₂—C₆H₄—COOH)—, —NHCH(CONHCH₂CH₂—C₆H₄—OCH₂COOH)—, —NHCH(CONH₂)— or —NHCH(pyrrolidinoyl)—.

Particularly preferred compounds of the formula I are the following:
N-[N-[N-(p-amidinobenzoyl)-β-alanyl]-L-α-aspartyl]-3-phenyl-L-alanine,
N-[N-[-4-(p-amidinobenzamido)butyryl]-L-α-aspartyl]-L-valine,
N-[N-(p-amidinobenzoyl)-β-alanyl]-β-alanine,
N-[N-[N-(p-amidinobenzoyl)-β-alanyl]-L-α-aspartyl]-L-leucine isopropyl ester,
N-[N-[N-(p-amidinobenzoyl)-β-alanyl]-L-α-aspartyl]-L-valine,
N-[N-[N-(p-amidinobenzoyl)-β-alanyl]-L-α-aspartyl]-3-(p-hydroxyphenyl)-L-alanine,
N-[N-[5-(p-amidinobenzamido)valeryl]-L-α-aspartyl]-3-phenyl-L-alanine,
isobutyl N-[5-(p-amidinobenzamido)valeryl]-L-α-aspartate,
N-[N-[N-(p-amidinobenzoyl)-β-alanyl]-L-α-aspartyl]-L-serine ethyl ester and
N-[N-[[(R)-1-(p-amidinobenzoyl)-3-pyrrolidinyl]-carbonyl]-L-α-aspartyl]-3-phenyl-L-alanine.

Further examples of compounds of the formula I are the following:
N-[N-[N-(1-amidino-4-piperidinylcarbonyl)-β-alanyl]-L-α-aspartyl]-3-phenyl-L-alanine,
N-[N-[N-(p-amidinophenylacetyl)-β-alanyl]-L-α-aspartyl]-3-phenyl-L-alanine,
N-[N-[4-(p-amidinophenylcarbamoyl)butyryl]-L-α-aspartyl]3-phenyl-L-alanine,
N-[N-[(p-amidinophenylcarbamoyl)acetyl]-L-α-aspartyl]-3-phenyl-L-alanine,
rac-N-[1-(p-amidinobenzoyl)-3-piperidinyl-carbonyl]-β-alanine,
N-[4-(p-amidinobenzamido)butyryl]-β-alanine,
N-[(DL)-N-(p-amidinobenzoyl)-3-phenyl-β-alanyl]-β-alanine,
N,N'-[[(S)-(p-amidinobenzamido)ethylene]dicarbonyl]-di-β-alanine,
2-N-(p-amidinobenzoyl)-4-N-(2-carboxyethyl)-L-asparagine,
N-[5-(p-amidinobenzamido)valeryl]-β-alanine,
rac-N-[[1-[3-(1-amidino-4-piperidinyl)propionyl]-3-piperidinyl]carbonyl]-β-alanine,
N-[[(S)-1-(p-amidinobenzoyl)-2-pyrrolidinyl]-acetyl]-β-alanine,
(S)-3-[[N-(p-amidinobenzoyl)-β-alanyl]amino-3-[(p-methoxyphenethyl)carbamoyl]propionic acid,
N-[[(R)-1-(p-amidinobenzoyl)-3-pyrrolidinyl]-carbonyl]-β-alanine,
N-[N-(p-amidinobenzoyl)-2-methyl-β-alanyl]-L-α-aspartamide,
N-[N-[(p-amidinophenyl)acetyl]-β-alanyl]-β-alanine,
rac-N-[[[1-(p-amidinophenyl)acetyl]-3-piperidinyl]-carbonyl]-β-alanine benzyl ester,
rac-N-[[1-[(p-amidinophenyl)acetyl]-3-piperidinyl]-carbonyl]-β-alanine,
N-[N-[N-[3-(1-amidino-4-piperidinyl)propionyl]-β-alanyl]-L-α-aspartyl]-3-phenyl-L-alanine,
(S)-β-[[DL-N-(p-amidinobenzoyl)-3-methyl-β-alanyl]amino]-γ-oxo-1-pyrrolidinebutyric acid,
DL-N-[N-(p-amidinobenzoyl)-β-alanyl]-3-methyl-β-alanine,
N-[DL-N-(p-amidinobenzoyl)-2-phenyl-β-alanyl]-β-alanine,
DL-N-[N-(p-amidinobenzoyl)-β-alanyl]-2-methyl-β-alanine,
DL-N-[N-(p-amidinobenzoyl)-β-alanyl]-2-phenyl-β-alanine,
p-[2-[[N-[N-(p-amidinobenzoyl)-β-alanyl]-L-α-aspartyl]-amino]ethyl]benzoic acid,
DL-N-[N-(p-amidinobenzoyl)-β-alanyl-3-phenyl-β-alanine,
[p-[2-[[N-[N-(p-amidinobenzoyl)-β-alanyl]-L-α-aspartyl]amino]ethyl]-phenoxy]acetic acid,
1-[N-(p-amidinobenzoyl)-β-alanyl]-4-piperidineacetic acid,
4-[N-(p-amidinobenzoyl)-β-alanyl]-1-piperazineacetic acid and
N-[N-[N-[(5-amidino-2-pyridyl)carbonyl]-β-alanyl]-L-α-aspartyl]-3-phenyl-L-alanine.

The above compounds can be obtained according to the invention by cleaving at least one protecting group from a compound of the formula

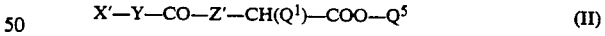

in which
$Q^1$ and Y have the meaning indicated further above,
$X'$ is phenyl or 4-piperidinyl which is substituted in the 4-position by an optionally protected amidino group, or $X'$ is 2- or 3-pyridyl which is substituted in the 5- or 6- position, respectively, by an optionally protected amidino group, and
$Z'$ and $Q^5$ have the same meaning as indicated further above for Z and $Q^2$, or
b) converting the nitrile group into the amidino group in a nitrile of the formula

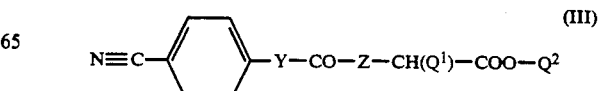

and, if desired, converting a compound of the formula I into a physiologically tolerable salt or converting a salt of a compound of the formula I into the free acid or base.

Examples of protecting groups in the compounds of the formula II are the benzyl or lower alkyl groups, such as t-butyl contained in the ester groups, benzyl—OCO— or t-Bu-OCO—; and amidino protecting groups, such as Z and Boc. Examples of protected amidino groups are —C(NH)NH—Z, —C(NH)NH-Boc and —C(N-Boc)-NH-Boc.

Ester groups can be cleaved in a manner known in the art, for example by hydrolysis using a base, such as an alkali metal hydroxide, for example sodium hydroxide, in a solvent, such as methanol. Benzyl esters can be cleaved by hydrogenation in the presence of a noble metal catalyst, such as palladium on carbon (Pd/C) in a solvent, such as methanol, ethanol, formic acid or acetic acid, at a temperature up to about 40° C., preferably at room temperature. In this process, an amidino protecting group present in the group X', such as Z, is removed at the same time.

Ester groups, such as t-butyl, or amidino protecting groups, such as Boc, can be cleaved, for example, using an acid, such as formic acid or trifluoroacetic acid, if desired in a solvent, such as dichloromethane, at a temperature up to 40° C., preferably at room temperature.

The compounds of the formula II are new and likewise a subject of the present invention. They can be prepared starting from known compounds by methods which are known to those skilled in the art, for example as described below.

In a first step, an amine of the formula $$H-Z'-CH(Q^1)COO-Q^{22}$$ IV is coupled with an acid of the formula $$R^5-NHCH(Q^{31})(CH_2)_{1-3}-COOH$$ Va, $$R^5-NHCH_2CH(Q^4)-COOH$$ Vb,

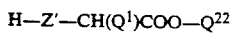 Vc

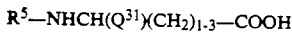 Vd

 Ve

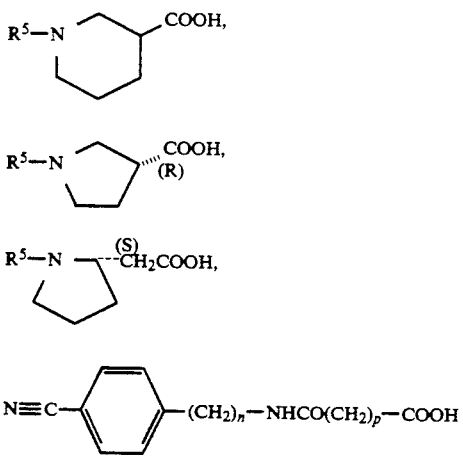 VI in which
$Q^{22}$ is an easily cleavable alkyl group,
$Q^{31}$ is hydrogen, methyl, phenyl, —COO—lower alkyl, or —CONH(CH$_2$)$_2$—COO-lower alkyl,
$R^5$ is an amino protecting group, such as Z or Boc, n=0 and p=3 or n=2 and p=1, An amide group is then obtained by methods known to those skilled in the art of peptide chemistry.

The coupling of a compound of formula IV with a compound of formula Va, Vb or VI can be carried out, for example, in tetrahydrofuran (THF) at −10° C. to room temperature under argon in the presence of O-benzotriazol-1-yl-N,N,N',N'-tetramethyluronium hexafluorophosphate (HBTU). The coupling of a compound of formula IV with a compound of formula Vc, Vd or Ve in THF using chlorodimethoxytriazine and N-methylmorpholine and then reacting the product with the p-toluenesulphonate of the amine of formula IV and N-methyl-morpholine.

From the reaction product thus obtained, an amino protecting group R$^5$, for example Z or Boc, can then be selectively removed as described above by catalytic hydrogenation or by means of trifluoroacetic acid.

An amine of the formula

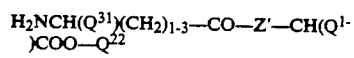 VIII obtained as above described, for example starting from compounds of formulae IV and Va, can then be coupled with 4-cyanobenzoic acid or 4-cyano-phenylacetic acid to give a nitrile, for example one of the formula III, for example as described above for the coupling of IV with Va.

A nitrile obtained in this way or a nitrile obtained by coupling IV and VI can be converted into a compound II in which X' contains a free amidino group, for example by reaction with hydrogen sulphide and triethylamine in pyridine to give the thioamide, methylation with methyl iodide in acetone and subsequent reaction with ammonium acetate in methanol. A nitrile of formula III can be converted analogously into the corresponding compound of the formula I.

An amine of the above formula VIII can also be reacted, for example, with 1-amidino-4-piperidinecarboxylic acid, p-amidinophenacetyl chloride or p-amidino-benzoyl chloride to give a compound II in which X' is 1-amidino-4-piperidinyl or p-amidinophenyl.

An amine of the formula VIII or an amine of the formulae Va to Ve obtained starting from a compound of the formula IV and an acid can furthermore be reacted in methylene chloride/aqueous sodium bicarbonate solution with p-amidinobenzoyl chloride and subsequently with benzyl chloroformate or with di-t-butyl dicarbonate in the presence of sodium carbonate to give a compound of the formula II in which X' is p-amidinophenyl protected by Z or Boc.

The compounds of the formulae IV–VI are known or can be prepared in analogy to the known compounds or as described in the examples below.

Thus, a nitrile of formula VI can be prepared by coupling the appropriate amine of the formula NCC$_6$H$_4$(CH$_2$)$_n$—NH$_2$ with the appropriate acid of the formula HOOC(CH$_2$)$_p$—COOQ$^{22}$, for example analogously to the coupling of an amine of formula IV with an acid of formula V, followed by removal of the ester group Q$^{22}$.

To prepare a compound of the formula II in which X' is 4-piperidinyl substituted in the 4-position by a protected amidino group, a compound of the formula

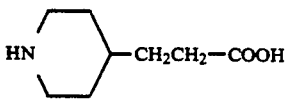  IX can first be reacted, for example, with N,N'-bis-(t-butoxycarbonyl)-S-methylisothiourea, in t-butanol and sodium hydroxide solution to give a compound of the formula

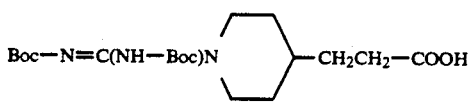  X and the latter can then be coupled, for example, with any one of the following compounds mour cells in that they inhibit metastasis formation thereof. They can thus also be employed as anti-tumour agents. They can further accelerate the healing of wounds.

The inhibition of fibrinogen formation on the fibrinogen receptor, glycoprotein IIb/IIIa, can be detected as follows:

Glycoprotein IIb/IIIa is obtained from Triton X-100 extracts of human blood platelets and purified by lectin affinity chromatography (Analytical Biochemistry 151, 1985, 169-177) and chromatography on an Arg-Gly-Asp-Ser affinity column (Science 231, 1986, 1559-62). The receptor protein thus obtained is bound to microtiter plates. The specific binding of fibrinogen to the immobilized receptor is determined with the aid of an ELISA system ("enzyme-linked immunosorbent assay"). The $IC_{50}$ values below correspond to the concentration of the test substance which is required in order to inhibit the binding of fibrinogen to the immobilised receptor by 50%:

| Product from Example: | 1 | 2 | 3 | 4 | 5 | 6 | 7 | 8 | 9 | 10 | 11 | 18 | 25 | 28 | 31 | 38 | 39 |
|---|---|---|---|---|---|---|---|---|---|---|---|---|---|---|---|---|---|
| $IC_{50}$ (μM) | 0.0003 | 0.13 | 0.045 | 0.035 | 0.01 | 0.01 | 0.027 | 0.10 | 0.005 | 0.022 | 0.0025 | 0.010 | 0.0067 | 0.005 | 0.0128 | 0.0036 | 0.0012 |

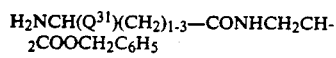  XIa

  XIb

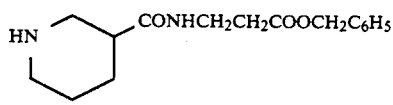  XIc

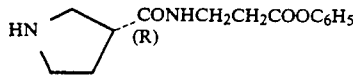  XId or

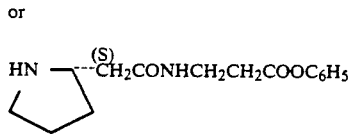  XIe in which $Q^{31}$ is hydrogen, methyl, phenyl, —COO-lower alkyl or —CONH(CH$_2$)$_2$—COO-lower alkyl.

A compound of the formula II in which X' is a phenyl or 4-piperidinyl which is substituted in the 4-position by a protected amidino group, can additionally be prepared by coupling an acid of the formula X'-Y-COOH with an amine of the above formula IV.

The compounds of the formula I, their solvates and their salts inhibit both the binding of fibrinogen, fibronectin and the Willebrand factor to the fibrinogen receptor of blood platelets (glycoprotein IIb/IIIa) and the binding thereof and of other adhesive proteins, such as vitronectine, collagen and laminine, to the corresponding receptors on the surface of different cell types. The said compounds thus influence cell-cell and cell-matrix interactions. They prevent in particular the formation of blood platelet thrombi and can be used in the control or prevention of diseases such as thrombosis, cerebral infarct, myocardial infarct, inflammation and arteriosclerosis. These compounds also have an effect on tu- As previously mentioned, the present invention also relates to medicaments containing a compound of the formula I, a solvate thereof or a salt thereof, and to a process for the production of medicaments of this type, which is characterised in that one or more of the said compounds and, if desired, one or more other therapeutically useful substances are brought into a pharmaceutical administration form. The medicaments can be administered enterally, for example orally in the form of tablets, film tablets, coated tablets, hard and soft gelatin capsules, solutions, emulsions or suspensions, or rectally, for example in the form of suppositories, or as a spray. The medicaments can also be administered parenterally, for example in the form of injection solutions or as an infusion.

For administration, these compounds can be mixed with pharmaceutically inert, inorganic or organic excipients. Lactose, corn flour or derivatives thereof, talc, stearic acid or its salts, for example, can be used as excipients of this type for tablets, coated tablets and hard gelatin capsules. Vegetable oils, waxes, fats, semi-solid and liquid polyols, for example, are suitable as excipients for soft gelatin capsules; depending on the nature of the active compound, however, no excipients at all are necessary in the case of soft gelatin capsules. Water, polyols, sucrose, invert sugar and glucose, for example, are suitable as excipients for the production of solutions and syrups, water, alcohols, polyols, glycerol and vegetable oils, for example, are suitable for injection solutions, and natural or hardened oils, waxes, fats and semi-solid or liquid polyols, for example, are suitable for suppositories. The pharmaceutical preparations of the invention can in also contain preservatives, solubilizers, stabilizers, wetting agents, emulsifiers, sweeteners, colorants, flavorings, salts for changing the osmotic pressure, buffers, coatings or antioxidants.

For the control or prevention of the diseases mentioned further above, the dosage of the active compound can vary within wide limits and is understood to be adjusted to the specific conditions in each individual case. In general, on oral administration a dose of from about 0.1 to about 20 mg/kg, preferably of about 0.5 to about 4 mg/kg, per day is suitable for adults. A larger dosage may also be appropriate depending on the condition being treated.

EXAMPLE 1

15 ml of trifluoroacetic acid were added to a suspension of 100 mg of N-[N-[N-(p-amidinobenzoyl)-$\beta$-alanyl]-3-(t-butoxycarbonyl)-L-alanyl]-3-phenyl-L-alanine t-butyl ester hydroiodide in 10 ml of dichloromethane. After 3 hours at room temperature, the solvents were evaporated over methanol/ethyl acetate. 32 mg of the trifluoroacetate of N-[N-[N-(p-amidino-benzoyl)-$\beta$-alanyl]-L-$\alpha$-aspartyl]-3-phenyl-L-alanine, m.p. 216°-220° C. (decomposition), were obtained.

The starting material can be prepared as follows:

a) 834 mg of HBTU and 0.24 ml of N-methylmorpholine were added at 0° C. under argon to a solution of 446 mg of Z-$\beta$-Al-a-OH and 785 mg of H-Asp(O-tBu)-Phe-O-tBu (obtained from the condensation of Z-Asp(O-tBu)-OH with H-Phe-O-tBu followed by hydrogenolysis). After 5 hours, the mixture was concentrated and the residue was partitioned in ethyl acetate/5% NaHCO$_3$. The organic phase was washed with water and 1M KHSO$_4$. The organic extracts were dried, filtered and concentrated. The residue was recrystallised from ethyl acetate/diisopropyl ether resulting in 592 mg of Z-$\beta$-Ala-Asp(O-tBu)-Phe-O-tBu, m.p. 138°-139° C.

b) By catalytic hydrogenation of the precursor (550 mg) in ethanol in the presence of 10% Pd/C, 417 mg of H-$\beta$-Ala-Asp(O-tBu)-Phe-O-tBu, MS: 464 (M+H)$^+$, were obtained after chromatography on silica gel using ethyl acetate/methanol 4:11:1.

c) By coupling 350 mg of the product from b) with 125 mg of 4-cyanobenzoic acid in the manner described in Example 1a), 293 mg of N-[3-(t-butoxycarbonyl)-N-[N-(p-cyanobenzoyl)-$\beta$-alanyl]-L-alanyl]-3-phenyl-L-alanine t-butyl ester, m.p. 74°-76° C., were isolated after chromato-graphy on silica gel using ethyl acetate.

d) A solution of 270 mg of the precursor in pyridine/triethylamine 15:1 was saturated with hydrogen sulphide. The solvents were removed after 24 hours and the residue was partitioned in ethyl acetate/5% NaHCO$_3$. The organic extracts were washed with water and with 1M potassium hydrogen sulphate solution, dried and con-centrated. After chromatography of the residue on silica gel using ethyl acetate followed by recrystallisation from hexane, 230 mg of N-sthiocarbamoylbenzoyl]-$\beta$-alanyl]-L-alanyl]-3-phenyl-L-alanine t-butyl ester, m.p. 101°-103° C., were obtained.

e) 2 ml of methyl iodide were added to a solution of 200 mg of the precursor in 15 ml of acetone. After 3 hours at boiling temperature, the mixture was allowed to cool to room temperature and the product was precipitated by addition of diethyl ether. 226 mg of N-[3-(t-butoxycarbonyl)-N-[N-[p-[1-(methylthio)formimidoyl]benzoyl]-$\beta$-alanyl]-L-alanyl]-3-phenyl-L-alanine t-butyl ester hydroiodide, m.p. 139°-140° C., were obtained.

f) 32 mg of ammonium acetate were added to a solution of 160 mg of the precursor in 10 ml of methanol. The reaction mixture was kept at boiling temperature for 4 hours. After cooling to room temperature, the solution was filtered, concentrated and treated with diethyl ether. The precipitated product was filtered off and dried yielding 135 mg of hydroiodide of N-[N-[N-(p-amidinobenzoyl)-$\beta$-alanyl]-3-(t-butoxycarbonyl)-L-alanyl]-3-phenyl-L-alanine t-butyl ester, m.p. 162°-163° C.

EXAMPLE 2

By treatment with trifluoroacetic acid in methylene chloride as described in Example 1 and after crys-tallisation from methanol/diethyl ether, 26 mg of N-[N-[N-(1-amidino-4-piperidinylcarbonyl)-$\beta$-alanyl]-L-$\alpha$-aspartyl]-3-phenyl-L-alanine trifluoroacetate (2:3), m.p. 127°-130° C., were obtained from 60 mg of N-[N-[N-(1-amidino-4-piperidinylcarbonyl)-$\beta$-alanyl]-3-(t-butoxycarbonyl)-L-alanyl]-3-phenyl-L-alanine t-butyl ester.

The starting material was prepared as follows:

Coupling 86 mg of 1-amidino-4-piperidine-carboxylic acid (Belg. Pat. 893,282, Nippon Chemiphar Co. Ltd.) with 119 mg of H-$\beta$-Ala-Asp(O-tBu)-Phe-O-tBu (Example 1b) in dioxane in the presence of 58 mg of pyridinium hydrochloride in the manner described in Example 1a) yielded 71 mg of N-[N-[NsL-alanyl]-3-phenyl-L-alanyl t-butyl ester, MS: 617 (M+H)$^+$, after chromatography on silica gel using methylene chloride/methanol 1:1.

EXAMPLE 3

By treatment with trifluoroacetic acid as described in Example 1, 36 mg of the trifluoroacetate of N-[N-[N-(p-amidinophenylacetyl)-$\beta$-alanyl]-L-$\alpha$-aspartyl]-3-phenyl-L-alanine, m.p. 218°-220° C. (from diethyl ether), were obtained from 50 mg of N-[N-[N-(p-amidinophenyl-acetyl)-$\beta$-alanyl]-3-(t-butoxycarbonyl)-L-alanyl]-3-phenyl-L-alanine t-butyl ester hydroiodide.

The starting material was prepared as follows:

a) 142 mg of 4-cyanophenylacetic acid were coupled with 371 mg of H-$\beta$-Ala-Asp(O-tBu)-Phe-O-tBu (Example 1b) in the manner described in Example 1a), yielding 250 mg of N-[N-[N-(p-cyanophenylacetyl)-$\beta$-alanyl]-3-t-butoxycarbonyl-L-alanyl]-3-phenyl-L-alanine t-butyl ester, m.p. 93°-94° C., after chromatography on silica gel using ethyl acetate/methanol.

b) Thionation of 230 mg of the precursor as described in Example 1d) yielded 160 mg of N-[N-[N-(p-thiocarbamoyl-phenylacetyl)-$\beta$-alanyl]-3-t-butoxycarbonyl-L-alanyl]-3-phenyl-L-alanine t-butyl ester, MS: 607 (M+H)$^+$, after chromatography on silica gel using ethyl acetate.

c) Methylation of 120 mg of the precursor analogously to Example 1e) resulted in 100 mg of N-[N-[N-(p-methylthio-formimidoyl)phenyl)acetyl]-$\beta$-alanyl]-3-t-butoxycarbonyl-L-alanyl]-3-phenyl-L-alanine t-butyl ester hydroiodide, m.p. 103°-104° C. (acetone/diethyl ether), after crystallization.

d) Reaction of 90 mg of the precursor with ammonium acetate as described in Example 1f) yielded 62 mg of N-[N-[N-(p-amidinophenyl-acetyl)-$\beta$-alanyl]-3-t-butoxycarbonyl-L-alanyl]-3-phenyl-L-alanine t-butyl ester hydroiodide, m.p. 152° C. (methanol/diethyl ether).

EXAMPLE 4

55 mg [N-[N-[4-(p-amidinophenyl-carbamoyl)-butyryl]-3-(t-butoxycarbonyl-alanyl]-3-phenyl-L-alanine t-butyl ester hydroiodide were treated with trifluoroacetic acid as described in Example 1, resulting in 31 mg of N-[N-[4-(p-amidinophenylcarbamoyl)butyryl]-L-$\alpha$-aspartyl]-3-phenyl-L-alanine trifluoroacetate (5:4), m.p. 159°–161° C., after crystallisation from ethanol/diethyl ether.

The starting material was prepared as follows:

a) By coupling 1.18 g of 4-aminobenzonitrile with 1.25 ml of monomethyl glutarate as described in Example 1a), 1.83 g of methyl 4-[(p-cyanophenyl)-carbamoyl]-butyrate, m.p. 126°–127° C., were obtained after recrystallisation from ethyl acetate.

b) 6 ml of 1N sodium hydroxide solution were added to a solution of 1 g of the precursor in 10 ml of methanol. After 7 hours, the reaction mixture was concentrated, the residue was extracted with ethyl acetate and the extract was then neutralized using 1N hydrochloric acid. The resulting precipitate was filtered off, washed with water and dried yielding 575 mg of 4-[(p-cyano-phenyl)carbamoyl]butyric acid, m.p. 200°–201° C.

c) 464 mg of the precursor were coupled with 863 mg of H-Asp(O-tBu)-Phe-O-tBu as described in Example 1a), yielding 701 mg of N-[3-(t-butoxycarbonyl)-N-[4-(p-cyanophenyl-carbamoyl)butyryl]-L-alanyl]-3-phenyl-L-alanine t-butyl ester, m.p. 64°–66° C. after chromatography on silica gel using ethyl acetate and subsequent stirring in hexane.

d) Reaction of 350 mg of the precursor with hydrogen sulphide in analogy to Example 1d) yielded 304 mg of N-[3-(t-butoxycarbonyl)-N-[4-(p-thio-carbamoyl-phenyl)-butyryl]-L-alanyl]-3-phenyl-L-alanine t-butyl ester, m.p. 178°–179° C., after recrystallisation from ethyl acetate.

e) Methylation of 150 mg of the precursor in analogy to Example 1e) yielded 175 mg of N-[3-(t-butoxycarbonyl)-N-[4-[[p-(1-(methylthio)-formimidoyl]-phenyl]carbamoyl]-butyryl]-L-alanyl]-3-phenyl-L-alanine t-butyl ester hydroiodide (1:1), m.p. 127°–128° C., after crystallisation using diethyl ether.

f) 60 mg of N-[N-[4-(p-amidinophenylcarbamoyl)-butyryl]-3-(t-butoxycarbonyl)-L-alanyl]-3-phenyl-L-alanine t-butyl ester hydroiodide, m.p. 130°–132° C., were then obtained from 90 mg of the precursor in analogy to Example 1f).

EXAMPLE 5

100 mg of N-[N-[(p-amidinophenethyl-carbamoyl)acetyl]-3-(t-butoxycarbonyl)-L-alanyl]-3-phenyl-L-alanine t-butyl ester hydroiodide were reacted with trifluoroacetic acid as described in Example 1 to give 69 mg of N-[N-[(p-amidinophenethylcarbamoyl)acetyl]-L-α-aspartyl]-3-phenyl-L-alanine trifluoroacetate, m.p. 141°–143° C., after crystal-lisation using diethyl ether.

The starting material was prepared as follows:

a) 370 mg of p-(2-aminoethyl)benzonitrile, MS: 147 (M+H)+, were obtained from 876 mg of p-cyanohydro-cinnamic acid (Pharmazie 28, 1973, 724) by a known reaction sequence (see Organic Synthesis 51, 1971, 48).

b) A solution of 0.59 ml of methyl malonyl chloride in 5 ml of THF was added dropwise at −10° C. to a solution of 731 mg of p-(2-aminoethyl)-benzonitrile and 1.39 ml of triethylamine in 10 ml of THF. The mixture was then allowed to warm to room temperature, and was then poured into ice water and adjusted to pH 2 with 1N hydrochloric acid. The THF was evaporated and the aqueous extracts were extracted with ethyl acetate. After drying and concentrating, 380 mg of methyl (p-cyanophenethyl)-malonamate, m.p. 125° C., were obtained.

c) Analogously to Example 4b), hydrolysis of 750 mg of the product from b) yielded 365 mg of N-(p-cyanophenethyl)malonamic acid, m.p. 137°–139° C.

d) Analogously to Example 1a), 352 mg of N-[3-(t-butoxycarbonyl)-N-[(p-cyanophenethylcarbamoyl)acetyl]-L-alanyl]-3-phenyl-L-alanine t-butyl ester, MS: 607 (M+H)+, was obtained by coupling 300 mg of the precursor with 507 mg of H-Asp(O-tBu)-Phe-O-tBu after chromatography on silica gel using ethyl acetate.

e) Analogously to Examples 1d), e) and f), the same reaction sequence using 380 mg of the product from d) yielded 152 mg of N-[N-[(p-amidino-phenethylcarbamoyl)-acetyl]-3-(t-butoxycarbonyl)-L-alanyl]-3-phenyl-L-alanine t-butyl ester hydroiodide, m.p. 91°–93° C. (decomposition), after crystallization using diisopropyl ether.

EXAMPLE 6

119 mg of the trifluoroacetate of N-[N-[4-(p-amidinobenzamido)butyryl]-L-α-aspartyl]-L-valine, m.p. 174° C. (decomposition), were obtained in analogy to Example 1 from 200 mg of N-[N-[4-(p-amidinobenzamido)-butyryl]-3-(t-butoxycarbonyl)-L-alanyl]-L-valine t-butyl ester hydroiodide after recrystallization from ethanol/diethyl ether.

The starting material can be prepared as follows:

a) By coupling 783 mg of Z-4-aminobutyric acid with 1 g of H-Asp(O-tBu)-Val-O-tBu (obtained from the condensation of Z-Asp(O-tBu)-OH with H-Val-O-tBu followed by hydrogenolysis) as described in Example 1a), 1.17 g of N-[N-[4-[1-(benzyloxy)formamido]butyramido]-3-(t-butoxycarbonyl)-L-alanyl]-L-valine t-butyl ester, m.p. 64°–65° C., were obtained after chromatography on silica gel using ethyl acetate and crystallisation using hexane.

b) Hydrogenolysis of 1.1 g of the precursor analogously to Example 1b) gave 1 g of N-[N-(4-aminobutyryl)-3-(t-butoxycarbonyl)-L-alanyl]-L-valine t-butyl ester, m.p. 99°–100° C.

c) A solution of 859 mg of the product from b) was added, after 2 hours at 0° C., to a solution of 324 mg of 4-cyanobenzoic acid, 352 mg of 2-chloro-4,6-dimethoxy-1,3,5-triazine and 0.24 ml of N-methylmorpholine in 10 ml of dimethylformamide. The mixture was allowed to warm to room temperature and 772 mg of N-[N-[4-(p-cyanobenz-amido)butyryl]-3-(t-butoxycarbonyl)-L-alanyl]-L-valine t-butyl ester, MS: 559 (M+H)+, were obtained after working up as in Example 1d) and after chromatography on silica gel using ethyl acetate.

d) 760 mg of the product from c) were subjected to the same reaction sequence as described in Examples 1d),e) and f), yielding 444 mg of N-[N-[4-(p-amidinobenzamido)-butyryl]-3-(t-butoxycarbonyl)-L-alanyl-L-valine t-butyl ester hydroiodide, m.p. 105°–107° C. (decomposition) after crystallization using diisopropyl ether.

EXAMPLE 7

1.09 g of rac-N-1-[[[p-[N-(benzyloxycarbonyl)amidino]benzoyl]-3-piperidinyl]carbonyl]-β-alanine benzyl ester and 0.25 g of Pd/C were stirred in 20 ml of acetic acid under hydrogen. The catalyst was filtered off and the filtrate was evaporated. The residue was taken up in water and the solution was evaporated. The precipitate was suspended in methanol, adjusted to pH 8 with ammonia and stirred, then filtered with suction, washed with methanol and dried. 530 mg of rac-N-[[1-(p-amidinobenzoyl)-3-piperi-dinyl]carbonyl]-β-alanine were obtained in the form of the hydrate (2:1), m.p. >265° C., MS: 347 (96, M+H).

The starting material was prepared as follows:

a) rac-N-(t-butoxycarbonyl)piperidine-3-carboxylic acid (Can. J. Physiol. Pharmacol. 57, 1979, 763) in THF was activated with chlorodimethoxytriazine and N-methyl-morpholine and then coupled with β-alanine benzyl ester p-toluenesulphonate (J. Org. Chem. 17, 1952, 1564) and N-methylmorpholine to give rac-N-[[1-(t-butoxycarbonyl)-3-piperidinyl]-carbonyl]-β-alanine benzyl ester, m.p. 57°–59° C.

b) By cleavage with trifluoroacetic acid, the tri-fluoroacetate of rac-(3-piperidinylcarbonyl)-β-alanine benzyl ester was obtained therefrom.

c) The product of b) was reacted in methylene chloride-/aqueous sodium bicarbonate solution with p-amidinobenzoylchloride and then with benzylchloroformate in the presence of sodium carbonate to give rac-N-1-[[[p-[N-(benzyloxycarbonyl)amidino]benzoyl]-3-piperidinyl]carbonyl]-β-alanine benzyl ester, MS: 571 (10, M+H).

EXAMPLE 8

512 mg of N-[4-p-[N-(benzyloxycarbonyl)amidino]-benzamido]-butyryl]-β-alanine benzyl ester and 170 mg of Pd/C in 10 ml of acetic acid were stirred under hydrogen. The catalyst was filtered off and the filtrate was evaporated. The residue was dissolved in water and the solution was evaporated. The residue was suspended in water, adjusted to pH 7 using ammonia, filtered with suction, washed with water and dried. 239 mg of N-[4-(p-amidinobenzamido)butyryl]-β-alanine, m.p. >250° C., MS: 321 (12, M+H), were obtained.

The starting material can be prepared as follows:

a) 4-(t-Butoxycarbonylamino)butyric acid in THF was activated with chlorodimethoxytriazine and N-methylmorpholine and reacted with β-alanine benzyl ester p-toluenesulphonate in the presence of N-methylmorpholine to give N-[4-(1-t-butoxyformamido)butyryl]-β-alanine benzyl ester, m.p. 54°–55° C.

b) From the above compound, in trifluoroacetic acid, the trifluoroacetate of N-(4-aminobutyryl)-β-alanine benzyl ester was obtained.

c) The latter was reacted in methylene chloride/-water/sodium hydrogen carbonate with p-amidinobenzoyl chloride and then with benzyl chloroformate in the presence of sodium carbonate to give N-[4-[p-[N-(benzyloxycarbonyl)amidino]benzamido]-butyryl]-β-alanine benzyl ester, m.p. 173°–183° C.

EXAMPLE 9

Analogously to Example 8, N-[N-(p-amidino-benzoyl)-β-alanyl]-β-alanine, m.p. >250° C., MS: 307 (6, M+H), was obtained in the form of the hydrate (2:1) from N-[N-p-[N-(benzyloxycarbonyl)amidino]benzoyl]-β-alanyl]-β-alanine benzylester.

The starting material was prepared as follows:

a) N-(t-butoxycarbonyl)-β-alanine and β-alanine benzyl ester were coupled analogously to the above examples to give N-[N-(t-butoxycarbonyl)-β-alanyl]-β-alanine benzyl ester, m.p. 84°–85° C.

b) The trifluoroacetate of (β-alanyl)-β-alanine benzyl ester was obtained therefrom in trifluoroacetic acid.

c) This compound was reacted with p-amidinobenzoyl chloride and subsequently with benzyl chloroformate to give N-[N-[p-[N-(benzyloxycarbonyl)amidino]-benzoyl]-β-alanyl]-β-alanine benzyl ester, m.p. 165°–166° C.

EXAMPLE 10

In analogy to Example 8, N-[(DL)-N-(p-amidinobenzoyl)-3-phenyl-β-alanyl]-β-alanine was obtained as the hydrate (3:1), m.p. >250° C., MS: 383 (62, M+H), from N-[(DL)-N-[p-[N-(benzyloxycarbonyl)amidino]benzoyl]-3-phenyl-β-alanyl]-β-alanine benzyl ester.

The starting material was prepared as follows:

a) DL-N-(t-butoxycarbonyl)-3-phenyl-β-alanine and β-alanine benzyl ester was coupled analogously to the above examples to give N-[(DL)-N-(t-butoxycarbonyl)-3-phenyl-β-alanyl]-β-alanine benzyl ester, m.p. 143°–144° C.

b) The trifluoroacetate of [(DL)-3-phenyl-β-alanyl]-β-alanine benzyl ester was obtained therefrom in trifluoroacetic acid.

c) This compound was reacted with p-amidinobenzoyl chloride and subsequently with benzyl chloroformate to give N-[(DL)-N-[p-[N-(benzyloxycarbonyl)amidino]benzoyl]-3-phenyl-β-alanyl-β-alanine benzyl ester, m.p. 187°–189° C.

EXAMPLE 11

443 mg of N-[3-[(benzyloxy)carbonyl]-N-[5-[p-[N-[(benzyloxy)-carbonyl]amidino]benzamido]valeryl]-L-alanyl]-3-phenyl-L-alanine benzyl ester and 111 mg of Pd/C in 9 ml of acetic acid were stirred under hydrogen gas for 3½ hours. The solution was filtered and evaporated, the residue was dissolved in water and the solution was again evaporated. The residue was stirred in water, filtered off with suction and dried. 246 mg of N-[N-[5-(p-amidinobenzamido)valeryl]-L-α-aspartyl]-3-phenyl-L-alanine, m.p. 241° C., was obtained as the hydrate (1:2).

The starting ester, m.p. 169°–171° C., was prepared as follows:

a) N-(t-butoxycarbonyl)-L-aspartic acid 4-benzyl ester was coupled with 3-phenyl-L-alanine benzyl ester to give N-[3-[(benzyloxy)carbonyl]-N-(t-butoxycarbonyl)-L-alanyl]-3-phenyl-L-alanine benzyl ester, m.p. 93°–94° C.

b) This compound was deprotected using trifluoroacetic acid and coupled with 5-(1-t-butoxyformamido)-valeric acid to give N-[3-[(benzyloxy)carbonyl]-N-[5-(1-t-butoxyformamido)-valeryl]-L-alanyl]-3-phenyl-L-alanine benzyl ester, m.p. 119.5°–120.5° C.

c) The compound of b) was then freed of the t-butoxycarbonyl protecting group in trifluoroacetic acid and then converted into the starting material in methylene chloride/water/sodium bicarbonate with p-amidinobenzoyl chloride and subsequently with benzyl chloroformate.

EXAMPLE 12

Analogously to Example 11, N,N'-[[(S)-(p-amidinobenzamido)-ethylene]dicarbonyl]di-β-alanine, m.p. >250° C., was obtained from N,N'-[[(S)-[p-[N-[(benzyloxy)carbonyl]amidino]benzamido]ethylene]-dicarbonyl]-di-β-alanine dibenzyl diester after evaporating with water and stirring with methanol.

The starting ester, m.p. 171°–172° C., was obtained as follows:

a) N-(t-butoxycarbonyl)-L-aspartic acid is coupled with two equivalents of β-alanine benzyl ester to give N,N'-[[(S)-(1-t-butoxyformamido)ethylene]dicarbonyl]di-β-alanine dibenzyl ester, m.p. 109°-110° C.

b) After cleavage of the t-butoxycarbonyl group with trifluoroacetic acid, the product was reacted in methylene chloride/aqueous sodium bicarbonate with p-amidinobenzoyl chloride and subsequently with benzyl chloroformate to give the starting ester.

EXAMPLE 13

Analogously to Example 11, 2-N-(p-amidino-benzoyl)-4-N-(2-carboxy-ethyl)-L-asparagine, m.p. 212° C. (dec.), was obtained from N-[(S)-N-[p-[N-[(benzyloxy)-carbonyl]amidino]benzoyl]-3-[(benzyloxy)carbonyl]β-alanyl]-β-alanine benzyl ester.

The starting ester was obtained as follows:
a) N-(t-butoxycarbonyl)-L-aspartic acid 1-benzyl ester was coupled with β-alanine benzyl ester to give 3-[[2-[(benzyloxy)carbonyl]ethyl]carbamoyl]-N-(t-butoxycarbonyl)-L-alanine benzyl ester, m.p. 77°-78° C.

b) After cleavage of the t-butoxycarbonyl protecting group in trifluoroacetic acid, the product was coupled in methylene chloride/water/sodium bicarbonate with p-amidinobenzoyl chloride and subsequently reacted with benzyl chloroformate to give the starting ester, m.p. 122°-123° C.

EXAMPLE 14

Analogously to Example 8, N-[5-(p-amidinobenzamido)valeryl]-β-alanine, m.p. >280° C., was obtained from N-[5-[p-[N-[(benzyloxy)-carbonyl]-amidino]benzamido]valeryl]-β-alanine benzyl ester.

The starting ester was prepared as follows:
a) 5-(1-t-butoxyformamido)valeric acid was coupled with β-alanine benzyl ester to give N-[5-(1-t-butoxyformamido)valeryl]-β-alanine benzyl ester, m.p. 69°-70° C.

b) The trifluoroacetate of N-(5-aminovaleryl)-β-alanine benzyl ester was obtained therefrom in trifluoroacetic acid.

c) Product b) above was reacted in methylene chloride/water in the presence of sodium bicarbonate with p-amidinobenzoyl chloride and subsequently with benzyl chloroformate to give the starting ester, m.p. 161°-161.5° C.

EXAMPLE 15

704 mg of rac-N-[[1-[3-[1-[(E/Z))-N,N'-bis(t-butoxycarbonyl)amidino]-4-piperidinyl]propionyl]-3-piperidinyl]carbonyl]-β-alaninbenzylester and 176 mg of Pd/C in 14.1 ml of formic acid were stirred under hydrogen for 18 hours. The catalyst was filtered off and washed with 1:1 formic acid/water. The filtrate was evaporated, the residue was dissolved in water and the solution was again evaporated. The residue was chromatographed using ethanol/methanol on silica gel. 254 mg of rac-N-[[1-[3-(1-amidino-4-piperidinyl)propionyl]-3-piperidinyl]carbonyl]-β-alanine, MS: 382 (100, M+H), were obtained.

The starting ester was prepared as follows:
a) 4-Piperidinopropionic acid was reacted with N,N'-bis(t-butoxycarbonyl)-S-methylisothiourea in t-butanol and 2N sodium hydroxide solution to give 3-[1-[(E/Z)-N,N'-bis(t-butoxycarbonyl)amidino]-4-piperidinyl]-propionic acid.

b) This was coupled with rac-N-(3-piperidinylcarbonyl)-β-alanine benzyl ester to give the starting ester, MS: 672 (12, M+H).

EXAMPLE 16

115 mg of N-[[(S)-1-[p-[N-[(benzyloxy)carbonyl]-amidino]benzoyl]-2-pyrrolidinyl]acetyl]-β-alanine and 50 mg of Pd/C were stirred under hydrogen for 4 hours in 2.5 ml of acetic acid. The catalyst was filtered off and the solution was evaporated. The residue was dissolved in water, evaporated again and chromatographed on silica gel using methanol. 46 mg of N-[[(S)-1-(p-amidino-benzoyl)-2-pyrrolidinyl]acetyl]-β-alanine, m.p. >250° C., are obtained.

The starting ester can be prepared as follows:
a) (S)-1-[(Benzyloxy)carbonyl]-2-pyrrolidinoacetic acid was coupled with β-alanine t-butyl ester to give N-[[(S)-1-[(benzyloxy)carbonyl]-2-pyrrolidinyl]acetyl]-β-alanine t-butyl ester, MS: 391 (69, M+H).

b) The acetate of N-[(2-pyrrolidinyl)acetyl]-β-alanine t-butyl ester was obtained therefrom by hydrogenation in acetic acid.

c) This was reacted in methylene chlorippresence of sodium bicarbonate with p-amidinobenzoyl chloride and subsequently with benzyl chloroformate to give N-[[(S)-1-[p-[N-[(benzyloxy)carbonyl]amidino]-benzoyl]-2-pyrrolidinyl]acetyl]-β-alanine t-butyl ester, m.p. 127°-128° C.

d) The starting ester, MS: 481 (100, M+H), was obtained therefrom in formic acid.

EXAMPLE 17

300 mg of benzyl-(S)-3-[[N-[p-[N-(t-butoxy-carbonyl)amidino]-benzoyl]-β-alanyl]amino]-3-[(p-methoxyphenethyl)carbamoyl]propionate and 75 mg of Pd/C were stirred under hydrogen for 4½ hours in 6 ml of formic acid. The catalyst was filtered off, the filtrate was evaporated, the residue was taken up in water and the solution was evaporated again. The crystalline substance was suspended in water, adjusted to pH 8 while stirring with ammonia and then filtered with suction. 151 mg of (S)-3-[[N-(p-amidino-benzoyl)-β-alanyl]amino-3-[(p-methoxyphenethyl)carbamoyl]-propionic acid was obtained as the hydrate (1:1), m.p. 217° C.

The starting ester was obtained as follows:
a) β-Alanine benzyl ester was reacted in methylene chloride/water sodium bicarbonate with p-amidinobenzoyl chloride and subsequently with di-t-butyl dicarbonate and sodium carbonate to give N-[p-[N-(t-butoxycarbonyl)amidino]benzoyl]-β-alanine benzyl ester, m.p. 127°-128° C.

b) N-[p-[N-(t-butoxycarbonyl)amidino]benzoyl]-β-alanine, MS: 336 (21, M+H), was obtained therefrom by catalytic hydrogenation.

c) N-(t-butoxycarbonyl)aspartic acid 4-benzyl ester was coupled with 2-(4-methoxyphenyl)ethylamine to t-butyl-[(S)-2-[(benzyloxy)carbonyl]-1-[(p-methoxyphenethyl)carbamoyl]ethyl]carbamate, m.p. 103°-104° C.

d) From this in trifluoroacetic acid was obtained the trifluoroacetate of 3-[(p-methoxyphenethyl)carbamoyl]-β-alanine benzyl ester.

e) The compound of d) was coupled with the product described in b) to give the starting ester, m.p. 150° C. (dec.).

EXAMPLE 18

Analogously to Example 8, N-[N-[N-(p-amidino-benzoyl)-β-alanyl]-L-α-aspartyl]-L-leucine isopropyl ester was obtained as the hydrate (1:1.3), m.p. 234° C. (dec.), from N-[3-[(benzyloxycarbonyl]-N-[N-[p-[N-[(benzyloxy)-carbonyl]amidino]benzoyl]-β-alanyl]-L-alanyl]-L-leucine isopropyl ester.

The starting ester was obtained in the following way:

a) N-(t-butoxycarbonyl)-L-leucine was converted into N-(t-butoxycarbonyl)-L-leucine isopropyl ester, $[\alpha]_D = -33°$ (MeOH, c=0.5), using dicyclohexylcarbodiimide, p-toluenesulphonic acid and isopropanol in pyridine.

b) The trifluoroacetate of L-leucine isopropyl ester was obtained therefrom in trifluoroacetic acid.

c) The compound of b) was coupled with N-(t-butoxycarbonyl)-L-aspartic acid 4-benzyl ester to give N-[3-[(benzyloxy)carbonyl]-N-(t-butoxycarbonyl)-L-alanyl]-L-leucine isopropyl ester, MS: 479 (25, M+H).

d) After cleavage of the t-butoxycarbonyl protecting group and coupling with N-(t-butoxycarbonyl)-β-alanine, N-[3-[(benzyloxy)carbonyl]-N-[N-(t-butoxycarbonyl)-β-alanyl]-L-alanyl]-L-leucine isopropyl ester, m.p. 103°-104° C., was obtained therefrom.

e) Compound d) was freed of the t-butoxycarbonyl protecting group in trifluoroacetic acid and then converted into the starting ester in methylene chloride/water/sodium bicarbonate with p-amidinobenzoyl chloride and subsequently using benzyl chloroformate, m.p. 176°-177° C.

EXAMPLE 19

Analogously to Example 8, N-[[(R)-1-(p-amidinobenzoyl)-3-pyrrolidinyl]carbonyl]-β-alanine was obtained as the hydrate (4:3), m.p.>250° C., $[\alpha]_D = -4.13°$ (1N HCl, c=0.46%), from N-[[(R)-1-[p-[N-[(benzyloxy)-carbonyl]amidino]benzoyl]-3-pyrrolidinyl]carbonyl]-β-alanine benzyl ester.

The starting ester was prepared in the following manner:

a) (R)-1-[(R)-α-methylbenzyl]-3-pyrrolidinomethanol, di-t-butyl dicarbonate and Pd/C in ethanol were stirred under hydrogen for 20 hours. t-Butyl (R)-3-(hydroxymethyl)-1-pyrrolidinocarboxylate, m.p. 35° C., $[\alpha]_D = +19.5°$ (methanol, c=1.0), was obtained.

b) From a) above, (R)-1-(t-butoxycarbonyl)-3-pyrrolidinocarboxylic acid, m.p. 135°-138° C., $[\alpha]_D = -15°$ (MeOH, c=1.0), was obtained using pyridinium dichromate in DMF.

c) Compound b) was coupled with β-alanine benzyl ester to give N-[[(R)-1-(t-butoxycarbonyl)-3-pyrrolidinyl]carbonyl]-β-alanine benzyl ester, m.p. 83°-84° C., $[\alpha]_D = -3.4°$ (MeOH, c=1.0).

d) The trifluoroacetate of N-[[(R)-3-pyrrolidinyl]carbonyl]-β-alanine benzyl ester was obtained therefrom in trifluoroacetic acid.

e) Compound d) was reacted in methylene chloride/water/sodium bicarbonate with p-amidinobenzoyl chloride and subsequently with benzyl chloroformate to give the starting ester, $[\alpha]_D = +2.2°$ (MeOH, c=0.5).

EXAMPLE 20

Analogously to Example 16, N-[N-(p-amidinobenzoyl)-2-methyl-β-alanyl]-L-α-aspartamide (2:1 epimers), m.p. 280° C., was obtained from benzyl (S)-3-[[D/L-N-[p-[N-[(benzyloxy)carbonyl]amidino]benzoyl]-2-methyl-β-alanyl]amino]succinamate.

The starting ester was prepared as follows:

a) Benzyl (S)-3-(1-t-butoxyformamido)succinamate was deprotected using trifluoroacetic acid and then coupled with DL-N-(t-butoxycarbonyl)-2-methyl-β-alanine to yield t-Butyl [(RS)-2-[[(S)-2-[(benzyloxy)carbonyl]-1-carbamoylethyl]-carbamoyl]propyl]carbamate, m.p. 135°-136° C.

b) After cleavage of the t-butoxycarbonyl protecting group in trifluoroacetic acid, the product was coupled in methylene chloride/water sodium bicarbonate with p-amidinobenzoyl chloride and finally reacted with benzyl chloroformate to give the starting ester (2:1 epimers), m.p. 178.5°-179.5° C.

EXAMPLE 21

548 mg of N-[N-[p-[N-(t-butoxycarbonyl)amidino]-phenyl]acetyl]-β-alanyl]-β-alanine benzyl ester were allowed to stand in 11 ml of formic acid for 18 hours. After addition of 137 mg of Pd/C, the mixture was stirred under hydrogen for 4 hours. The catalyst was filtered off and the filtrate was evaporated. The residue was dissolved in water and the solution was evaporated again. The residue was suspended in water and adjusted to pH 8 using ammonia, then filtered with suction and dried. 290 mg of N-[N-[(p-amidinophenyl)acetyl]-β-alanyl]-β-alanine were obtained as the hydrate (1:1), m.p. 286° C. (dec.).

The starting material, m.p. 262° C. (dec.), was obtained by reaction of N-(β-alanyl)-β-alanine benzyl ester in DMF/tri-ethylamine with p-amidinophenylacetyl chloride and subsequent reaction with di-t-butyl dicarbonate.

EXAMPLE 22

535 mg of rac-N-[[1-[p-[N-(t-butoxycarbonyl)amidino]phenylacetyl]-3-piperidinyl]carbonyl]-β-alanine benzyl ester was allowed to stand in 11 ml of formic acid for 19 hours. The solvent was evaporated, and the residue was evaporated with water and recrystallized from acetonitrile. 340 mg of rac-N-[[[1-(p-amidinophenyl)acetyl]-3-piperidinyl]carbonyl]-β-alanine benzyl ester formate (1:1), m.p. 97°-98° C., were obtained.

The starting ester, MS: 551 (9, M+H), was obtained by coupling rac-N-[(3-piperidinyl)carbonyl]-β-alanine benzyl ester in DMF/triethylamine with p-amidinophenylacetyl chloride and subsequent reaction with di-t-butyl dicarbonate.

EXAMPLE 23

535 mg of rac-N-[[1-[p-[N-(t-butoxycarbonyl)amidino]phenylacetyl]-3-piperdinyl]carbonyl]-β-alanine benzyl ester were allowed to stand in 11 ml of formic acid for 19 hours, and the mixture was treated with 134 mg of Pd/C and stirred under hydrogen for 4 hours. The solution was filtered and evaporated, the residue was dissolved in water and the solution was evaporated again. The product was stirred in acetonitrile, filtered with suction and dried, yielding 272 mg of rac-N-[[1-[(p-amidinophenyl)acetyl]-3-piperidinyl]carbonyl]-β-alanine, MS: 361 (41, M+H).

EXAMPLE 24

1127 mg of N-[3-[(benzyloxy)carbonyl]-N-[N-[3-[1-[(E or Z)-N,N'-bis(t-butoxycarbonyl)amidino]-4-piperidinyl]propionyl]-β-alanyl]-L-alanyl]-3-phenyl-L-alanine benzyl ester were allowed to stand in 22.5 ml of formic acid for 21 hours. After addition of 282 mg of Pd/C, the mixture was stirred under hydrogen for 5 hours. The solution was filtered and evaporated, the residue was dissolved in water and the solution was evaporated again. The residue was stirred in water, filtered with suction and dried to yield 543 mg of N-[N-

[N-[3-(1-amidino-4-piperidinyl)propionyl]-β-alanyl]-L-α-aspartyl]-3-phenyl-L-alanine, m.p. 246° C. (dec.).

The starting ester was prepared as follows:

a) N-(t-butoxycarbonyl)-β-alanine was coupled with N-[3-[(benzyloxy)-carbonyl]-L-alanyl]-3-phenyl-L-alanine benzyl ester to give N-[3-[(benzyloxy)carbonyl]-N-[N-(t-butoxycarbonyl)-β-alanyl]-L-alanyl]-3-phenyl-L-alanine benzyl ester, m.p. 124°-125° C.

b) The t-butoxycarbonyl protecting group of product a) was cleaved and, the product was coupled with 3-[1-[N,N'-bis-(t-butoxycarbonyl)amidino]-4-piperidinyl]-propionic acid to give the starting ester, 1:1 ethyl acetate solvate, m.p. 100° C. (dec.).

EXAMPLE 25

1.3 g of 3-[(benzyloxy)carbonyl]-N-[5-[p-[N-[(benzyloxy)carbonyl]-amidino]benzamido]valeryl]-L-alanine isobutyl ester and 325 mg of Pd/C in 25 ml of acetic acid were stirred under hydrogen for 5½ hours. The solution was filtered and evaporated and the residue was evaporated successively with water, methanol and ethanol. The resulting product was adjusted to pH 8 in acetonitrile using ammonia, stirred and filtered with suction. 596 mg of isobutyl N-[5-(p-amidinobenzamido)-valeryl]-L-α-aspartate were obtained as the hydrate (1:1), m.p. 162°-166° C.

The starting ester, m.p. 127.5°-129.5° C., was prepared as follows:

a) Benzyl N-(t-butoxycarbonyl)-L-α-aspartate was converted into the N-(t-butoxycarbonyl)-3-[(benzyloxy)-carbonyl]-L-alanine isobutyl ester, MS: 323 (8, M—$C_4H_8$), using dicyclohexylcarbodiimide, p-toluenesulphonic acid and isobutyl alcohol in pyridine.

b) After cleavage of the t-butoxycarbonyl group in trifluoroacetic acid, the product was coupled with 5-(1-t-butoxyformamido)valeric acid to give 3-[(benzyloxy)carbonyl]-N-[5-(1-t-butoxyformamido)-valeryl]-L-alanine isobutyl ester, m.p. 64°-66° C.

c) Product b) was deprotected using trifluoroacetic acid and then reacted in methylene chloride/water/sodium bicarbonate with p-amidinobenzoyl chloride and subsequently with benzyl chloroformate to give the starting ester.

EXAMPLE 26

562 mg of benzyl (S)-β-[[DL-N-[p-[N-[(benzyloxy)-carbonyl]amidino]-benzoyl]-3-methyl-β-alanyl]amino]-γ-oxo-1-pyrrolidinobutyrate and 140 mg of Pd/C in 11 ml of acetic acid were stirred under hydrogen for 2 hours. The filtered solution was evaporated and the residue was evaporated successively with water, methanol and ethanol. The residue was finally adjusted to pH 8 in ethanol using ammonia, stirred and filtered off with suction yielding 289 mg of (S)-β-[[DL-N-(p-amidinobenzoyl)-3-methyl-β-alanyl]amino]-γ-oxo-1-pyrroli-dinobutyric acid are as the hydrate (2:3), m.p. 222°-224° C.

The starting ester was prepared in the following way:

a) Benzyl (S)-β-(1-t-butoxyformamido)-γ-oxo-1-pyrrolidinobutyrate was deprotected using trifluoroacetic acid and coupled with (RS)-3-(1-t-butoxyformamido)butyric acid to give benzyl (S)-β-[(RS)-3-(3-(1-t-butoxyformamido)-butyramido]-γ-oxo-1-pyrrolidinobutyrate, m.p. 104°-105° C.

b) The starting ester, MS: 642 (100, M+H), was obtained from compound a) obtained by cleaving the t-butoxycarbonyl group in trifluoroacetic acid and reacting with p-amidinobenzoyl chloride and subsequently with benzyl chloroformate in methylene chloride/water/sodium bicarbonate.

EXAMPLE 27

Analogously to Example 8, DL-N-[N-(p-amidinobenzoyl)-β-alanyl]-3-methyl-β-alanine was obtained as the hydrate (3:1) m.p. 291° C. (dec.), from DL-N-[N-[p-[N-[(benzyloxy)carbonyl]amidino]benzoyl]-β-alanyl]-3-methyl-β-alanine benzyl ester.

The starting ester, m.p. 179°-180° C., was prepared as follows:

a) N-(t-butoxycarbonyl)-β-alanine was coupled with DL-3-aminobutyric acid benzyl ester to give DL-N-[N-(t-butoxycarbonyl)-β-alanyl]-3-methyl-β-alanine benzyl ester, m.p. 70°-72° C.

b) DL-N-(β-alanyl)-3-methyl-β-alanine benzyl ester was obtained from compound a) by using trifluoroacetic acid.

c) Compound b) was then reacted in methylene chloride/water/sodium bicarbonate with p-amidinobenzoyl chloride and subsequently with benzyl chloroformate to give the starting ester.

EXAMPLE 28

Analogously to Example 8, N-[N-[N-(p-amidinobenzoyl)-β-alanyl]-L-α-aspartyl]-L-serine ethyl ester was obtained as the hydrate (2:7), m.p. 201°-203° C., from N-[3-[(benzyloxy)carbonyl]-N-[N-[p-[N-[(benzyloxy)-carbonyl]-amidino]benzoyl]-β-alanyl]-L-serine ethyl ester.

The starting ester, m.p. 177°-179° C., was prepared as follows:

a) Benzyl-N-(t-butoxycarbonyl)-L-α-aspartate was coupled with L-serine ethyl ester to give N-[3-[(benzyloxy)carbonyl]-N-(t-butoxycarbonyl)-L-alanyl]-L-serine ethyl ester, m.p. 96°-97° C.

b) After cleavage of the t-butoxycarbonyl group, the product was coupled with N-(t-butoxycarbonyl)-β-alanine to give N-[3-[(benzyloxy)-carbonyl]-N-[N-(t-butoxycarbonyl)-β-alanyl]-L-alanyl]-L-serine ethyl ester, m.p. 132°-134° C.

c) Compound b) was deprotected in trifluoroacetic acid and the product was subsequently reacted in methylene chloride/water/sodium bicarbonate with p-amidinobenzoyl chloride and finally with benzyl chloroformate to give the starting ester.

EXAMPLE 29

Analogously to Example 8, N-[DL-N-(p-amidinobenzoyl)-2-phenyl-β-alanyl]-β-alanine was obtained as the hydrate (4:1), m.p. 276° C., from N-[N-[p-[DL-N-[(benzyloxy)carbonyl]amidino]benzoyl]-2-phenyl-β-alanyl]-β-alanine benzyl ester.

The starting ester, m.p. 173°-174° C., was prepared as follows:

a) DL-2-phenyl-β-alanine was reacted with di-t-butyl dicarbonate in t-butanol and sodium hydroxide solution to give DL-N-(t-butoxycarbonyl)-2-phenyl-β-alanine, m.p. 147°-148° C.

b) Compound a) was coupled with β-alanine benzyl ester to give N-[DL-N-(t-butoxycarbonyl)-2-phenyl-β-alanyl]-β-alaninebenzyl ester, m.p. 115°-116° C.

c) After cleavage of the protecting group of compound b), the product was reacted in methylene chloride/water/sodium bicarbonate with p-amidino-benzoyl chloride and subsequently with benzyl chloroformate to give the starting ester.

EXAMPLE 30

Analogously to Example 8, DL-N-[N-(p-amidinobenzoyl)-β-alanyl]-2-methyl-β-alanine was obtained as the hydrate (3:1), m.p. >300° C., from N-[N-[p-[N-[(benzyloxy)carbonyl]amidino]benzoyl]-β-alanyl]-DL-2-methyl-β-alanine benzyl ester.

The starting ester, m.p. 159°-160° C., was obtained as follows:

a) N-(t-butoxycarbonyl)-β-alanine was coupled with [DL-2-methyl-β-alanine benzyl ester to give DL-N-[N-(t-butoxycarbonyl)-β-alanyl]-2-methyl-β-alanine benzyl ester, MS: 365 (47, M+H).

b) After cleavage of the protecting group from compound a), the product was reacted in methylene chloride/water/sodium bicarbonate with p-amidinobenzoyl chloride and subsequently with benzyl chloroformate to give the starting ester.

EXAMPLE 31

Analogously to Example 11, N-[N-[[(R)-1-(p-amidinobenzoyl)-3-pyrrolidinyl]carbonyl]-L-α-aspartyl]-3-phenyl-L-alanine acetate (2:1) was obtained as the hydrate (3:2), m.p. 215° C., from N-[N-[[(R)-1-[p-[N-[(benzyloxy)carbonyl]amidino]benzoyl]-3-pyrrolidinyl]carbonyl]-3-[(benzyloxy)-carbonyl]-L-alanyl]-3-phenyl-L-alanine benzyl ester after evaporating with water and stirring in ethanol.

The starting ester was obtained as follows:

a) (R)-1-(t-butoxycarbonyl)-3-pyrrolidinocarboxylic acid was coupled with N-[3-[(benzyloxy)carbonyl]-L-alanyl]-3-phenyl-L-alanine benzyl ester to give N-[N-[[(R)-1-(t-butoxycarbonyl)-3-pyrrolidinyl]carbonyl]-3-[(benzyloxy)-carbonyl]-L-alanyl]-3-phenyl-L-alanine benzyl ester, m.p. 84°-85° C.

b) The t-butoxycarbonyl group in compound a) was removed in trifluoroacetic acid and the product was reacted in methylene chloride/water/sodium bicarbonate with p-amidinobenzoyl chloride and subsequently with benzyl chloroformate to give the starting ester, m.p. 144°-145° C.

EXAMPLE 32

Analogously to Example 7, DL-N-[N-(p-amidinobenzoyl)-β-alanyl]-2-phenyl-β-alanine was obtained as the hydrate (1:1), m.p. 243°-245° C., from N-[N-[p-[N-[(benzyoxy)carbonyl]amidino]benzoyl]-β-alanyl]-DL-2-phenyl-β-alanine benzyl ester.

The starting ester was obtained as follows:

a) N-(t-butoxycarbonyl)-2-phenyl-β-alanine was heated to reflux in acetone with benzyl bromide and potassium carbonate for 17 hours to yield DL-N-(t-butoxycarbonyl)-2-phenyl-β-alanine benzyl ester, m.p. 58°-59° C.

b) After cleavage of the t-butoxycarbonyl group, the product was coupled with N-(t-butoxycarbonyl)-β-alanine to give DL-N-[N-(t-butoxycarbonyl)-β-alanyl]-2-phenyl-β-alanine benzyl ester, m.p. 84.5°-86° C.

c) Compound b) was converted into the trifluoroacetate of the N-(β-alanyl)-2-phenyl-β-alanine benzyl ester in trifluoroacetic acid.

d) The latter is reacted in methylene chloride/water/sodium bicarbonate with p-amidinobenzoyl chloride and subsequently with benzyl chloroformate to give the starting ester, m.p. 165°-166° C.

EXAMPLE 33

Analogously to Example 11, p-[2-[[N-[N-(p-amidinobenzoyl)-β-alanyl]-L-α-aspartyl]amino]ethyl]-benzoic acid was obtained as the hydrate (3:7), m.p. 194°-196° C. (methanol/water), from benzyl p-[2-[[3-[(benzyloxy)carbonyl]-N-[N-[p-[N-[(benzyloxy)carbonyl]amidino]-benzoyl]-β-alanyl]-L-alanyl]amino]ethyl]benzoate.

The starting ester, m.p. 162°-163° C., was prepared as follows:

a) p-(2-chloroethyl)benzoyl chloride was converted into benzyl p-(2-chloroethyl)benzoate, MS: 274 (8, M), using benzyl alcohol and pyridine in methylene chloride.

b) Benzyl p-(2-azidoethyl)benzoate, MS: 281 (2, M) was obtained therefrom using sodium azide in DMSO.

c) This was reacted in pyridine with triphenylphosphine and subsequently with conc. ammonia to give benzyl p-(2-aminoethyl)-benzoate, MS: 226 (16, M—CH₂NH).

d) Benzyl p-[2-[[3-[(benzyloxy)carbonyl]-N-(t-butoxycarbonyl)-L-alanyl]amino]ethyl]benzoate, m.p. 99°-100° C., was obtained therefrom by coupling with benzyl N-(t-butoxycarbonyl)-L-α-aspartate.

e) Compound d) was deprotected in trifluoroacetic acid and coupled with N-(t-butoxycarbonyl)-β-alanine to give p-[2-[[3-[(benzyloxy)carbonyl]-N-[N-(t-butoxycarbonyl)-β-alanyl]-L-alanyl]amino]ethyl]benzoate, m.p. 138°-139° C.

f) After cleavage of the t-butoxycarbonyl group in trifluoroacetic acid, the product was reacted in methylene chloride/water/sodium bicarbonate with p-amidinobenzoyl chloride and subsequently with benzyl chloroformate to give the starting ester.

EXAMPLE 34

Analogously to Example 7, [DL-N-[N-(p-amidinobenzoyl)-β-alanyl-3-phenyl-β-alanine was obtained as the hydrate (3:1), m.p. 220° C. (dec.), from DL-N-[N-[p-[N-[(benzyloxy)carbonyl]amidino]benzoyl]-β-alanyl]-3-phenyl-β-alanine benzyl ester.

The starting ester, m.p. 208° C., was obtained as follows:

a) N-(t-butoxycarbonyl)-β-alanine was reacted with DL-3-phenyl-β-alanine benzyl ester to give DL-N-[N-(t-butoxycarbonyl)-β-alanyl]-3-phenyl-β-alanine benzyl ester, m.p. 124.5°-126° C.

b) The trifluoroacetate of DL-N-(β-alanyl)-3-phenyl-β-alanine benzyl ester was obtained therefrom in trifluoroacetic acid.

c) This was reacted in methylene chloride/water/sodium bicarbonate with p-amidinobenzoyl chloride and subsequently with benzyl chloroformate to give the starting ester.

EXAMPLE 35

Analogously to Example 11, [p-[2-[[N-[N-(p-amidinobenzoyl)-β-alanyl]-L-α-aspartyl]amino]ethyl]phenoxy]acetic acid is obtained as the hydrate (2:7), m.p. 210°-213° C., from benzyl (S)-3-[[N-[p-[N-[(benzyloxy)-carbonyl]amidino]benzoyl]-β-alanyl]amino]-N-[p-[[(benzyloxy)carbonyl]-methoxy]phenethyl]succinamate.

The starting ester, m.p. 172°-174° C., was prepared as follows:

a) t-Butyl [2-(4-hydroxyphenyl)ethyl]carbamate, benzyl bromoacetate and potassium carbonate were heated in acetone. t-Butyl [p-[[(benzyloxy)-carbonyl]methoxy]phenethyl]carbamate, MS: 385 (0.5, M), was obtained.

b) After cleavage of the t-butoxycarbonyl protecting group, the product was coupled with N-(t-butoxycarbonyl)aspartic acid-4-benzyl ester to give benzyl (S)-N-[p-[[(benzyloxy)carbonyl]methoxy]phenethyl]-3-[1-t-butoxyformamido]-succinamate, m.p. 178.5°–180.5° C.

c) Product b) was deprotected in trifluoroacetic acid and coupled with N-(t-butoxycarbonyl)-β-alanine to give t-butyl [2-[[(S)-2-[(benzyloxy)-carbonyl]-1-[[p-[[(benzyloxy)carbonyl]methoxy]phenethyl]carbamoyl]-ethyl]carbamoyl]-ethyl]carbamate, m.p. 123°–124° C.

d) After cleavage of the t-butoxycarbonyl protecting group, the product was reacted in methylene chloride/water/sodium bicarbonate with p-amidino-benzoyl chloride and subsequently with benzyl chloroformate to give the starting ester.

EXAMPLE 36 a) A solution of 280 mg of 1-[N-(p-cyanobenzoyl)-β-alanyl]-4-piperidinoacetic acid and 1 ml of triethylamine in 15 ml of pyridine was saturated with hydrogen sulphide. After 36 hours, the solution was evaporated and the residue was suspended in ethyl acetate/water. Filtration and drying of the insoluble material gave 255 mg of 1-[N-[p-(thiocarbamoyl)-benzoyl]-β-alanyl]-4-piperidinoacetic acid.

b) A solution of 150 mg of the precursor in 15 ml of acetone was heated to boiling temperature with 1 ml of methyl iodide for 3 hours. After cooling the solution to room temperature, 130 mg of 1-[N-[p-[1-(methylthio)formimidoyl]benzoyl]-β-alanyl]-4-piperidinoacetic acid hydroiodide (1:1), m.p. 206°–207° C., precipitate.

c) 100 mg of 1-[N-[p-[1-(methylthio)formimidoyl]-benzoyl]-β-alanyl]-4-piperidinoacetic acid and 30 mg ammonium acetate in 10 ml of methanol were kept at boiling temperature for 3 hours. After cooling to room temperature, the solution was filtered, concentrated and treated with diethyl ether. The precipitated oil was chromatographed on silica gel RP 18 using water/methanol (10:1) after decanting of the solvent. 24 mg of 1-[N-(p-amidino-benzoyl)-β-alanyl]-4-piperidinoacetic acid hydroiodide (10:1), m.p. 206° C., were obtained.

The starting nitrile was obtained as follows:

a) 4.96 g of 4-cyanobenzoyl chloride and 2.67 g of β-alanine were stirred at room temperature for 4 hours in 450 ml of sodium bicarbonate solution (2%) and the mixture was acidified using concentrated sulphuric acid (pH 6). The solution was evaporated and extracted using ethyl acetate. Drying and evaporation of the organic phase gave a residue which, with diisopropyl ether, yielded 4.69 g of N-(p-cyanobenzoyl)-β-alanine, m.p. 155°–157° C.

b) Coupling of 635 mg of N-(p-cyanobenzoyl)-β-alanine with 540 mg of 4-piperidinoacetic acid gave, after chromatography on silica gel RP 18 using THF/water (85:15), 300 mg of 1-[N-(p-cyanobenzoyl)-β-alanyl]-4-piperidinoacetic acid, MS: 344 (M+H)+.

EXAMPLE 37

400 mg of t-butyl 4-[N-(p-amidinobenzoyl)-β-alanyl]-1-piperazinoacetate were stirred in 15 ml of methylene chloride and 15 ml of trifluoroacetic acid. The solution was evaporated, the residue was suspended in 5 ml of ethanol and the undissolved material was filtered off. The filtrate was treated with ethyl acetate and the precipitate was filtered with suction and dried. Chromatography of the crude product on silica gel RP 18 using water yielded to 38 mg of 4-[N-(p-amidinobenzoyl)-β-alanyl]-1-piperazinoacetic acid trifluoroacetate (5:8), m.p. 157°–158° C.

The starting material was prepared as follows:

a) 2.23 g of N-benzyloxycarbonyl-β-alanine was coupled with 2.58 g of piperazine. The evaporation residue was suspended in THF, the undissolved material was filtered off and the filtrate was evaporated. Chromatography of the residue on silica gel RP 18 using water/methanol (2–5%) gave 2.51 g of benzyl [2-(4-piperazinylcarbonyl)ethyl]carbamate, MS: 291 (M+).

b) 600 mg of compound a), 0.3 ml of t-butyl bromoacetate and 25 mg of tetrabutylammonium hydrogen sulphate were dissolved in 10 ml of toluene and stirred with 10 ml of 50% strength sodium hydroxide solution for 1 hour. The organic phase was washed with water and evaporated. Chromatography of the residue on silica gel using ethyl acetate/methanol (9:1) gave 480 mg of t-butyl 4-[N-[(benzyloxy)carbonyl]-β-alanyl]-1-piperazinoacetate, MS: 406 (M+H)+.

c) Compound b) was then hydrogenated in ethanol for 1 hour in the presence of 200 mg of Pd/C. The catalyst was filtered off and the filtrate was evaporated. 290 mg of t-butyl 4-β-alanyl-1-piperazinoacetate, MS: 271 (M+), were obtained.

d) Compound c) and 341 mg of p-amidinobenzoyl chloride were stirred in 20 ml of methylene chloride and 10 ml of saturated sodium bicarbonate. The organic phase was separated off and evaporated, and the residue was suspended in ethyl acetate. Filtration with suction and drying of the crystals yielded 400 mg of t-butyl 4-[N-(p-amidinobenzoyl)-β-alanyl]-1-piperazino-acetate, MS: 418 (M+H)+.

EXAMPLE 38

Analogously to Example 37, 1.6 g of N-[N-[N-(p-amidinobenzoyl)-β-alanyl]-3-(t-butoxycarbonyl)-L-alanyl]-L-valine t-butyl ester were deprotected. The crude product was chromatographed on silica gel RP 18 using water/THF (95:5). 867 mg of N-[N-[N-(p-amidinobenzoyl)-β-alanyl]-L-α-aspartyl]-L-valinetrifluoroacetate, m.p. 162°–163° C., were obtained.

The starting ester was prepared as follows:

a) t-Butyl N-benzyloxycarbonyl-L-α-aspartate and L-valine t-butyl ester hydrochloride were coupled to give N-[N-[(benzyloxy)carbonyl]-3-(t-butoxycarbonyl)-L-alanyl]-L-valine t-butyl ester, m.p. 75° C. (d).

b) Compound a) was deprotected analogously to Example 37c. N-[3-t-butoxycarbonyl)-L-alanyl]-L-valine t-butyl ester, m.p. 71° C., was obtained.

c) 2.8 g of compound b) were coupled with 1.78 g of N-[(benzyloxy)-carbonyl]-β-alanine and the crude product was chromatographed on silica gel using ethyl acetate to yield 2.24 g of N-[N-[N-[(benzyloxy)-carbonyl]-β-alanyl]-3-(t-butoxycarbonyl)-L-alanyl]-L-valine t-butyl ester, m.p. 126° C.

d) Deprotection of 2.2 g of compound c) analogously to Example 37c) yielded 1.61 g of N-[N-β-alanyl-3-(t-butoxycarbonyl)-L-alanyl]-L-valine t-butyl ester.

e) Reaction of 1 g of p-amidinobenzoyl chloride with 1.61 g of compound d) according to procedure 37d gave 1.62 g of starting ester.

EXAMPLE 39

Analogously to Example 37, 1.4 g of N-[N-[N-(p-amidinobenzoyl)-β-alanyl]-3-(t-butoxycarbonyl)-L-alanyl]-3-(p-t-butoxyphenyl)-L-alanine t-butyl ester were deprotected. The product was suspended in ethanol, insoluble material was filtered off and the filtrate was treated with ether. Filtration with suction and washing of the precipitate with 20 ml of isopropanol/ethanol (1:1) gave 801 mg of N-[N-[N-(p-amidinobenzoyl)-β-alanyl]-L-β-aspartyl]-3-(p-hydroxyphenyl)-L-alanine trifluoroacetate (2:5), m.p. 202°-204° C.

The starting ester was prepared as follows:

a) N-[(9H-fluoren-9-yloxy)carbonyl]-3-(t-butoxycarbonyl)-L-alanine and 3-(p-t-butoxyphenyl)-L-alanine t-butyl ester were coupled to give N-[N-[(9H-fluoren-9-yloxy)carbonyl]-3-(t-butoxycarbonyl)-L-alanyl]-3-(p-t-butoxyphenyl)-L-alanine t-butyl ester and 5 ml of piperidine and the reaction solution was evaporated. The residue was suspended in methanol and insoluble material was filtered off. The filtrate was evaporated and chromatographed on silica gel using ethyl acetate to yield 2 g of 3-(t-butoxyphenyl)-N-[3-(p-t-butoxycarbonyl)-L-alanyl]-L-alanine t-butyl ester.

c) Compound a) was coupled with 0.96 g of N-benzyloxycarbonyl-β-alanine and the crude product was chromatographed on silica gel using ethyl acetate to yield 2.23 g of N-[N-[N-[(benzyloxy)carbonyl]-β-alanyl]-3-(t-butoxycarbonyl)-L-alanyl]-3-(p-t-butoxyphenyl)-L-alanine t-butyl ester, MS: 670 (M+H)+.

d) Deprotection of 2.1 g of the precursor (compound c)) as in Example 37c) gave 1.67 g of N-[N-β-alanyl]-3-(t-butoxycarbonyl)-L-alanyl]-3-(p-t-butoxyphenyl)-L-alanine t-butyl ester, MS: 536 (M+H)+.

e) Coupling of 1.5 g of compound d) with 0.6 g of p-amidinobenzoyl chloride as in Example 37d) gave 1.6 g of starting ester, MS: 682 (M+H)+.

EXAMPLE 40

Analogously to Example 24, N-[N-[N-[(5-amidino-2-pyridyl)carbonyl]-β-alanyl]-L-α-aspartyl]-3-phenyl-L-alanine, m.p. 222°-223° C. (dec.), was obtained from the corresponding ester.

The starting ester was prepared as follows:

a) N-[3-[(Benzyloxy)carbonyl]-N-[N-[N-(t-butoxycarbonyl)-β-alanyl]-L-alanyl]-3-phenyl-L-alanine benzyl ester was deprotected and coupled with 5-cyano-2-pyridinecarboxylic acid to give N-[3-[(benzyloxy)carbonyl]-N-[N-[(5-cyano-2-pyridyl)carbonyl]-β-alanyl]-L-alanyl]-3-phenyl-L-alanine benzyl ester, m.p. 157°-158° C.

b) Compound a) was converted as in Example 36a) into N-[3-[(benzyloxy)carbonyl]-N-[N-[[5-(thiocarbamoyl)-2-pyridyl]carbonyl]-β-alanyl]-L-alanyl]-3-phenyl-L-alanine benzyl ester, m.p. 131°-132° C.

c) Compound b) was converted as in Example 36b) and c) into N-[3-[(benzyloxy)carbonyl]-N-[N-[[5-[N-(t-butoxycarbonyl)amidino]-2-pyridyl]-carbonyl]-β-alanyl]-L-alanyl]-3-phenyl-L-alanine benzyl ester, MS: 779 (11,M+H).

EXAMPLE A

Compounds of formula I can be used in a manner known to those skilled in the art as the active compounds for the production of tablets of the following composition:

|  | per tablet |
|---|---|
| Active compound | 200 mg |
| microcrystalline cellulose | 155 mg |
| corn flour | 25 mg |
| talc | 25 mg |
| hydroxypropylmethylcellulose | 20 mg |
|  | 425 mg |

EXAMPLE B

Compounds of formula I can also be used in a manner known to those skilled in the art as the active compounds in the production of capsules of the following composition:

|  | per capsule |
|---|---|
| Active compound | 100.0 mg |
| corn flour | 20.0 mg |
| lactose | 5.0 mg |
| talc | 4.5 mg |
| magnesium stearate | 0.5 mg |
|  | 220.0 mg |

We claim:

1. An acetic acid derivative of formula $$H_2N-\overset{NH}{\underset{}{\overset{\|}{C}}}-X-Y-\overset{O}{\underset{}{\overset{\|}{C}}}-Z-\overset{H}{\underset{Q^1}{\overset{|}{C}}}-\overset{O}{\overset{\|}{C}}-O-Q^2 \quad (I)$$

in which $Q^1$ is hydrogen, methyl or phenyl, $Q^2$ is hydrogen, phenyl-lower alkyl or lower alkyl which can be cleaved under physiological conditions, X is 1,4-phenylene, 1,4-piperidinylene bound via the C atom in the 4-position to the group Y, or 2,5- or 3,6-pyridylene, Y is a group of the formula $$-(CH_2)_{0-2}-\overset{O}{\overset{\|}{C}}-\overset{H}{\underset{}{\overset{|}{N}}}-\overset{H}{\underset{Q^3}{\overset{|}{C}}}-(CH_2)_{1-3}- \quad (Y^1)$$

$$-\overset{O}{\overset{\|}{C}}-\overset{H}{\underset{}{\overset{|}{N}}}-\overset{H}{\underset{H}{\overset{|}{C}}}-\overset{H}{\underset{Q^4}{\overset{|}{C}}}- \quad (Y^2)$$

$-(CH_2)_2-NHCOCH_2-$  (Y³)

$-NHCO(CH_2)_3-$  (Y⁴)

$$-(CH_2)_{0-2}-\overset{O}{\overset{\|}{C}}-N\diagdown\diagup \quad (Y^5)$$

$$\overset{O}{\diagdown}{C-N}\diagdown\diagup_{(R)} \quad (Y^6)$$

-continued $$\text{(Y}^7\text{)}$$

[structure: pyrrolidine ring with C(=O)–N and CH₂ substituent]

Q³ is hydrogen, methyl, phenyl, —COOH, —COO-lower alkyl, —CONH(CH₂)₂—COOH or CONH(CH₂)₂—COO-lower alkyl, Q⁴ is hydrogen, methyl or phenyl, Z is a 1,4-piperazinylene group, a 1,4-piperidinylene group bound via the N-atom in the 1 position to the CO group, or a group of the formula:

—NHCH(R¹)— or —NHCH(COR²)—

R¹ is hydrogen, methyl, phenyl or —COO-lower alkyl,

R² is the radical of an α-aminocarboxylic acid bound via the amino group or an ester or amide thereof, or a group of the formula —NHCH₂CH₂—Ar or —CO—R² is an optionally mono- or di-lower-alkylated carbamoyl group or a pyrrolidinoyl or piperidinoyl group, Ar is phenyl or phenyl which is substituted by lower alkyl, lower alkoxy, —COOH, —COO-lower alkyl, —O(CH₂)₁₋₄—COOH, —O(CH₂)₁₋₄—COO-lower alkyl, —CONH2, —CONH-lower alkyl, —CON(lower alkyl)2, pyrrolidinoyl or piperidinoyl, and hydrates or solvates and physiologically acceptable salts thereof.

2. A compound according to claim 1 having the formula $$\text{H}_2\text{N(HN)C—X—Y}^a\text{—CONHCH(R}^{11}\text{)CH}_2\text{COOQ}^{21}$$   I-A in which X is 1,4-phenylene or 1,4-piperidinylene bound via the C atom in the 4-position to the group Y$^a$, Y$^a$ is a group of the formula $$-(CH_2)_{0-1}-\overset{O}{\overset{\|}{C}}-\overset{H}{\overset{|}{N}}-\overset{H}{\underset{Q^a}{\overset{|}{C}}}-(CH_2)_{1-2}-$$   (Y¹¹)

—(CH₂)₂—NHCOCH₂—   (Y³)

—NHCO(CH₂)₃—   (Y⁴)

$$\text{(Y}^{51}\text{)}$$

[structure: piperidine ring with C(=O)–N]

Q$^a$ is hydrogen or phenyl,

R¹¹ is hydrogen or —CO—R²²

R²² is the radical of an α-aminocarboxylic acid bound via the amino group or of an ester or amide thereof, and Q²¹ is hydrogen or lower alkyl which can be cleaved under physiological conditions, and hydrates or solvates and physiologically acceptable salts thereof.

3. The compound of claim 1, in which Y is a group selected from

—CONH(CH₂)₂₋₄—,
—CH₂CONH(CH₂)₂—,
—CONHCH(C₆H₅)CH₂—,
—CONHCH(CONHCH₂CH₂COOH)CH₂—,
—CONHCH(COOH)CH₂— and
—CONHCH(CH₃)CH₂—.

4. The compound of claim 1 in which Z is a group selected from —NHCH₂—, —NHCH(CH₃)—, —NHCH(C₆H₅)—, —NHCH(COO-isobutyl)—, —NHCH(C₆H₅)—, —NHCH(CO-Val)—, —NHCH(CO-Phe)—, —NHCH(CO-Tyr)-, —NHCH(CO-Ser-OC₂H₅)—, —NHCH(CO-Leu-O-iso-propyl)—, —NHCH(CONHCH₂CH₂—C₆H₄—OCH₃)—, —NHCH(CONHCH₂CH₂—C₆H₄—COOH)—, —NHCH(CONHCH₂CH₂—C₆H₄—OCH₂COOH)—, —NHCH(CONH₂)— or —NHCH(pyrrolidinoyl)—.

5. The compound of claim 2 selected from the group consisting of:

N-[N-[4-(p-amidinobenzamido)butyryl]-L-α-aspartyl]-L-valine,

N-[N-(p-amidinobenzoyl)-β-alanyl]-β-alanine and

N-[N-[N-(p-amidinobenzoyl)-62 -alanyl]-L-α-aspartyl]-3-phenyl-L-alanine.

6. The compound of claim 2 selected from the group consisting of:

N-[N-[N-(1-amidino-4-piperidinylcarbonyl)-β-alanyl]-L-α-aspartyl]-3-phenyl-L-alanine, N-[N-[N-(p-amidinophenylacetyl)-β-alanyl]-L-α-aspartyl]-3-phenyl-L-alanine, N-[N-[4-(p-amidinophenylcarbamoyl)butyryl]-L-α-aspartyl]-3-phenyl-L-alanine, N-[N-[(p-amidinophenylcarbamoyl)acetyl]-L-α-aspartyl]-3-phenyl-L-alanine, rac-N-[1-(p-amidinobenzoyl)-3-piperidinylcarbonyl]-β-alanine, N-[4-(p-amidinobenzamido)butyryl]-β-alanine and N-[(DL)-N-(p-amidinobenzoyl)-3-phenyl-β-alanyl]-β-alanine.

7. A compound according to claim 1 selected from the group consisting of:

N-[N-[N-(p-amidinobenzoyl)-β-alanyl]-L-α-aspartyl]-L-leucine isopropyl ester,

N-[N-[N-(p-amidinobenzoyl)-β-alanyl]-L-α-aspartyl]-L-valine,

N-[N-[N-(p-amidinobenzoyl)-β-alanyl]-L-α-aspartyl]-3-(p-hydroxyphenyl)-L-alanine, N-[N-[5-(p-amidinobenzamido)valeryl]-L-α-aspartyl]-3-phenyl-L-alanine, isobutyl N-[5-(p-amidinobenzamido)valeryl]-L-α-aspartate, N-[N-[N-(p-amidinobenzoyl)-β-alanyl]-L-α-aspartyl]-L-serine ethyl ester and N-[N-[[(R)-1-(p-amidinobenzoyl)-3-pyrrolidinyl]carbonyl]-L-α-aspartyl]-3-phenyl-L-alanine.

8. A compound according to claim 1 selected from the group consisting of:

N,N'-[[(S)-(p-amidinobenzamido)ethylene]dicarbonyl]-di-β-alanine,

2-N-(p-amidinobenzoyl)-4-N-(2-carboxyethyl)-L-asparagine,

N-[5-(p-amidinobenzamido)valeryl]-β-alanine, rac-N-[[1-[3-(1-amidino-4-piperidinyl)propionyl]-3-piperidinyl]carbonyl]-β-alanine, N-[[(S)-1-(p-amidinobenzoyl)-2-pyrrolidinyl]acetyl]-β-alanine, (S)-3-[[N-(p-amidinobenzoyl)-β-alanyl]amino-3-[(p-methoxyphenethyl)carbamoyl]propionic acid, N-[[(R)-1-(p-amidinobenzoyl)-3-pyrrolidinyl]carbonyl]-β-alanine,
N-[N-(p-amidinobenzoyl)-2-methyl-β-alanyl]-L-α-aspartamide,
N-[N-[(p-amidinophenyl)acetyl]-β-alanyl]-β-alanine,
rac-N-[[[1-(p-amidinophenyl)acetyl]-3-piperidinyl]-carbonyl]-β-alanine benzyl ester,
rac-N-[[1-[(p-amidinophenyl)acetyl]-3-piperidinyl]-carbonyl]-β-alanine,
N-[N-[N-[3-(1-amidino-4-piperidinyl)propionyl]-β-alanyl]-L-α-aspartyl]-3-phenyl-L-alanine,
(S)-β-[[DL-N-(p-amidinobenzoyl)-3-methyl-β-alanyl-]amino]-γ-oxo-1-pyrrolidinebutyric acid,
DL-N-[N-(p-amidinobenzoyl)-β-alanyl]-3-methyl-β-alanine,
N-[DL-N-(p-amidinobenzoyl)-2-phenyl-β-alanyl]-β-alanine,
DL-N-[N-(p-amidinobenzoyl)-β-alanyl]-2-methyl-β-alanine,
DL-N-[N-(p-amidinobenzoyl)-β-alanyl]-2-phenyl-β-alanine,
p-[2-[[N-[N-(p-amidinobenzoyl)-β-alanyl]-L-α-aspartyl]-amino]ethyl]-benzoic acid,
DL-N-(p-amidinobenzoyl)-β-alanyl-3-phenyl-β-alanine,
[p-[2-[[N-[N-(p-amidinobenzoyl)-β-alanyl]-L-α-aspartyl]amino]-ethyl]phenoxy]acetic acid,
1-[N-(p-amidinobenzoyl)-β-alanyl]-4-piperidineacetic acid,
4-[N-(p-amidinobenzoyl)-β-alanyl]-1-piperazineacetic acid and
N-[N-[N-[(5-amidino-2-pyridyl)carbonyl]-β-alanyl]-L-α-aspartyl]-3-phenyl-L-alanine.

9. A pharmaceutical composition comprising as an active ingredient an effective amount of a compound of claim 1.

10. A acetic acid derivative of formula

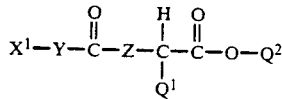

in which

X¹ is phenyl or 4-piperidinyl substituted in the 4-position by an optionally protected amidino group, or X¹ is 2- or 3-pyridyl which is substituted in the 5- or 6-position, respectively, by an optionally protected amidino group, Y is a group of the formula:

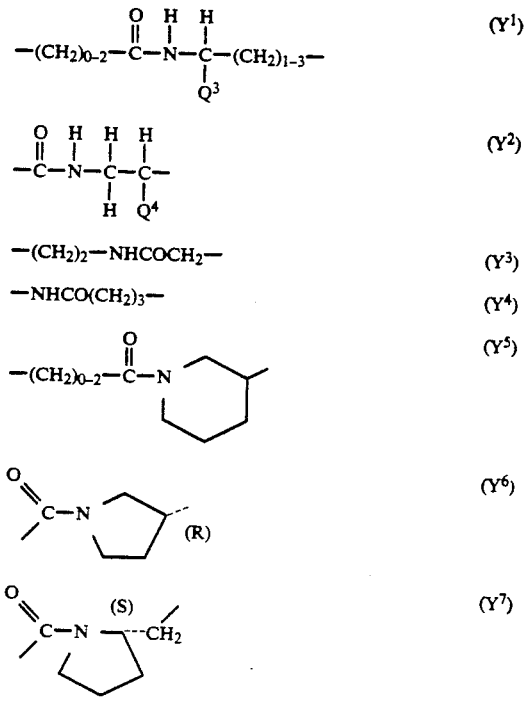

Z is a 1,4-piperazinylene group, a 1,4-piperidinylene group bound via the N atom in the 1-position to the CO group, or a a group of the formula

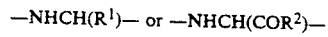

Q¹ is hydrogen, methyl or phenyl,
Q² is hydrogen, phenyl-lower alkyl or lower alkyl which can be cleaved under physiological conditions,
Q³ is hydrogen, methyl, phenyl, —COOH, —COO-lower alkyl, —CONH(CH₂)₂—COOH or —CONH((CH₂)₂—COO-lower alkyl,
Q⁴ is hydrogen, methyl or phenyl,
R¹ is hydrogen, methyl, phenyl or —COO-lower alkyl, and
R² is —NHCH₂CH₂—Ar or
—CO—R² is, optionally, mono- or di-lower alkylated carbamoyl group or a pyrrolidinoyl or piperidinoyl group.

and which compound has at least one easily cleavable ester group or protected amidino group.

* * * * *

UNITED STATES PATENT AND TRADEMARK OFFICE
CERTIFICATE OF CORRECTION

PATENT NO. : 5,273,982

DATED : December 18, 1993

INVENTOR(S) : Alig, et al.

It is certified that error appears in the above-identified patent and that said Letters Patent is hereby corrected as shown below:

Claim 1, Column 27, line 5, please delete the formula and replace it with the formula below:

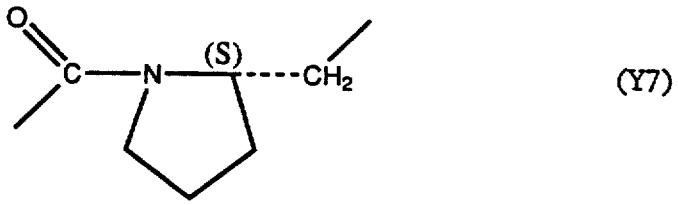

(Y7)

Claim 1, Column 27, lines 20-21, please delete the phrase "the radical of an α-aminocarboxylic acid bound via the amino group or an ester or amide thereof, or".

Claim 1, Column 27, line 30, please delete "(lower alkyl)2" and substitute therefor "(lower alkyl)$_2$".

Claim 2, Column 27, line 37, please delete:

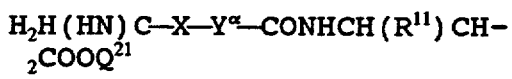

1-A and insert therefor:

1-A

UNITED STATES PATENT AND TRADEMARK OFFICE
CERTIFICATE OF CORRECTION

PATENT NO. : 5,273,982

DATED : December 18, 1993

INVENTOR(S) : Alig, et al.

It is certified that error appears in the above-identified patent and that said Letters Patent is hereby corrected as shown below:

Claim 5, Column 28, line 23, delete "62", and insert "ß".

Claim 8, Column 29, line 12-13, please delete:

(S)-ß-[[DL-N-(p-amidinobenzoyl)-3-methyl-ß-alanyl-
    ]-amino]-γ-oxo-1-pyrrolidinebutyric acid, and insert therefor:

(S)-ß-[[DL-N-(p-amidinobenzoyl)-3-methyl-ß-alanyl]-
    amino]-γ-oxo-1-pyrrolidinebutyric acid, Claim 10, Column 30, line 48, please delete "group." and insert therefor "group,".

Signed and Sealed this

Twenty-third Day of May, 1995

Attest:

BRUCE LEHMAN

Attesting Officer     Commissioner of Patents and Trademarks